(12) United States Patent
Sanger et al.

(10) Patent No.: US 7,966,195 B2
(45) Date of Patent: Jun. 21, 2011

(54) SYSTEM AND METHOD FOR PROVIDING OPTIMIZED MEDICAL ORDER SETS

(75) Inventors: Philip A. Sanger, Austin, TX (US); Charles Robertson, Richmond, VA (US); Robert Weathersby, Rye, NH (US)

(73) Assignee: Intercede Health, Houston, TX (US)

( * ) Notice: Subject to any disclaimer, the term of this patent is extended or adjusted under 35 U.S.C. 154(b) by 689 days.

(21) Appl. No.: 11/776,499

(22) Filed: Jul. 11, 2007

(65) Prior Publication Data

US 2009/0018862 A1    Jan. 15, 2009

(51) Int. Cl.
*G06Q 50/00* (2006.01)
*G06Q 10/00* (2006.01)
(52) U.S. Cl. .............................................. 705/2; 705/3
(58) Field of Classification Search ....................... 705/2
See application file for complete search history.

(56) References Cited

U.S. PATENT DOCUMENTS

| | | | |
|---|---|---|---|
| 5,583,758 A * | 12/1996 | McIlroy et al. | 705/2 |
| 5,786,816 A * | 7/1998 | Macrae et al. | 715/837 |
| 6,769,568 B2 | 8/2004 | Bonini et al. | |
| 2005/0033603 A1 | 2/2005 | Suzuki et al. | |
| 2005/0197545 A1 | 9/2005 | Hoggle | |
| 2005/0246200 A1 | 11/2005 | Thomson et al. | |
| 2006/0122869 A9 | 6/2006 | Rosenfeld et al. | |
| 2006/0287885 A1 | 12/2006 | Frick | |

OTHER PUBLICATIONS

Berner, Performance of Four Computer-Based Diagnostic Systems, vol. 330:1792-1796, Jun. 23, 1994 No. 25.*
Sharkey, Michael. "Setting Sail," www.HealthExecutive.com, Oct. 2005, pp. 12-17.
Advertisement for Order Optimizer, www.orderoptimizer.com, May 2006.

* cited by examiner

*Primary Examiner* — Luke Gilligan
*Assistant Examiner* — Tran Nguyen
(74) *Attorney, Agent, or Firm* — Vinson & Elkins LLP

(57) ABSTRACT

System and method for preparing patient order sets by an attending physician include optimization of orders particularly when multiple diagnoses are being treated.

18 Claims, 40 Drawing Sheets

The next step is to map the new Basic Info Module to the new Order Set Template for Depression.

SYSTEM AND METHOD FOR PROVIDING OPTIMIZED MEDICAL ORDER SETS

CROSS-REFERENCE TO RELATED APPLICATIONS

N/A

STATEMENT REGARDING FEDERALLY SPONSORED RESEARCH OR DEVELOPMENT

N/A

SUMMARY

The present disclosure provides systems and methods that are applied to the treatment or management of medical patients, and can be advantageously applied to producing treatment orders for the management of patient treatment in a hospital or clinical setting, and are particularly advantageous for care of patients with multiple diagnoses. The disclosed systems and methods are described in terms of preferred embodiments, the management of a physician group of hospitalists, for example. Hospitalists are physicians who focus their practice on inpatient care, being the physicians of record for a patient while in the hospital, and transitioning the patient back to the care of his or her primary care physician upon discharge from the hospital. One aspect of inpatient care is that there are often multiple diagnoses for a particular patient. The present disclosure provides systems and methods that process best practice protocols from evidence based medicine and produce an optimized order set for the treatment of a patient with a single diagnosis or with multiple diagnoses, thus providing better and more efficient care in a clinical setting.

An aspect of the disclosure is improved systems and methods for producing order sets for an attending physician. As used herein order sets are a collection of evidence-based treatment protocols for specific medical conditions. The systems and methods include a set of computer readable instructions, termed Order Optimizer by the present inventors that merges and organizes treatment protocols in situations where multiple conditions are diagnosed. This merging provides a concise, legible, and medically appropriate representation of a physician's "next steps" in patient treatment.

In certain embodiments the system allows administrative users to create order sets. The system uses a taxonomy to create the attributes of order sets. The taxonomy is as follows.

a. An element is the atomic unit of document content. Elements must be combined to provide meaningful value, but are powerful through their ability to be reused and recombined. Examples of elements can include a single letter or word, punctuation mark, or symbol such as a checkbox.

b. An item is a combination of elements into a discrete entity. Items can be unique or reused, and are generally organized with other items of similar context to allow users to make choices. Examples of items can include a single sentence, drug name, or directive, or survey question.

c. Item categories are collections of items associated with a narrowly defined theme. Item categories allow users to make a choice, or review a list of entities having a common relationship. Example of categories are pharmaceutical agents, laboratory tests, or survey questions.

d. Modules are the grouping of multiple entities into sections, each section representing a broad theme. Examples of modules are a book's chapter, a list of all medications and lab work for a merged set of diagnoses, or a group of survey questions on a similar topic.

e. An order set is the unique combination of descriptive information for a particular subject. Examples of order sets are a complete book, an Admission Order Set, or a complete survey.

Throughout this disclosure, unless the context dictates otherwise, the word "comprise" or variations such as "comprises" or "comprising," is understood to mean "includes, but is not limited to" such that other elements that are not explicitly mentioned may also be included. Further, unless the context dictates otherwise, use of the term "a" may mean a singular object or element, or it may mean a plurality, or one or more such objects or elements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

The present disclosure can be described in certain embodiments as an electronic system for providing medical orders for a patient, wherein the system comprises a user interface such as a desktop or portable computer that includes at least a processor, a monitor and a user input device, such as a keyboard, mouse, and/or a voice recognition device. As used herein the "client" refers to the health care provider, either a physician such as a hospitalist or other doctor treating the patient, or it can also refer in some cases to the hospital, institution, or practice group where or with whom the doctor practices. The "patient" is the individual being treated by the client, as would be the normal use of that term.

Figure 1:
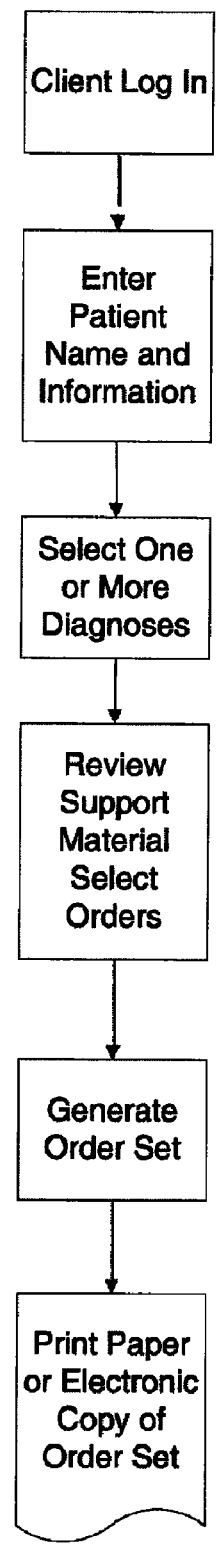
FIG. 1 is a flow diagram of an embodiment of the invention as presented to a user on the user interface.

A simplified overview of the use of the system is shown in FIG. 1. A client, typically a physician or medical provider, upon entering the system sees a login page, where the user name and password are entered and authenticated. On the next display a patient's name and information are entered and a user selects one or more diagnoses for that patient. The user is then presented with lists of orders and decision support materials associated with the designated diagnoses. The user reviews the lists and selects those orders and information that are appropriate for the patient. The user then requests the system to generate an order set, which can be reviewed, edited and/or printed either in hard copy or electronic form.

Figure 2:
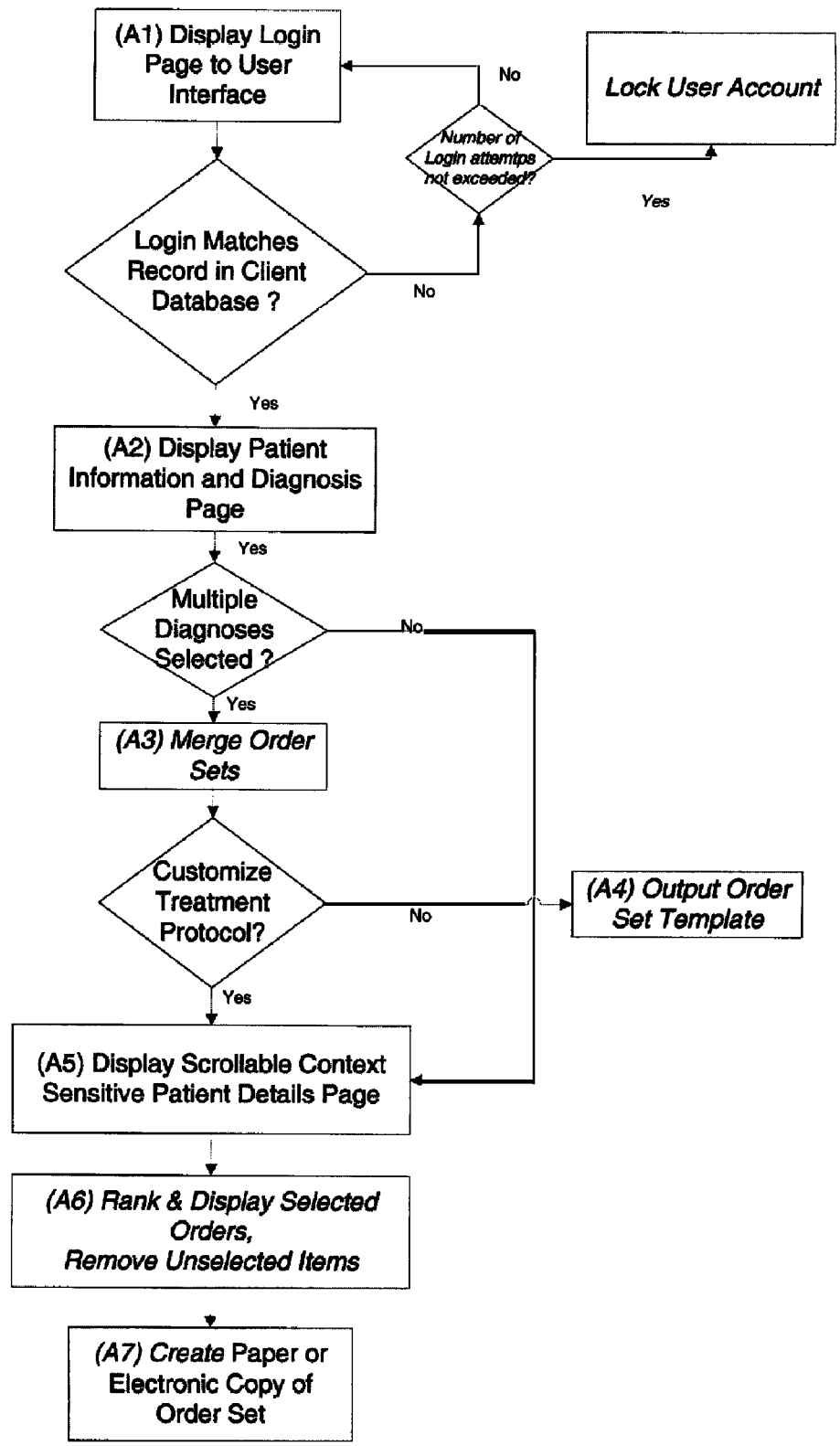
FIG. 2 is a flow diagram of use of the system to create an order set.

A flow diagram of system interaction with a user is shown as FIG. 2. The system first displays a login page to the user interface and receives login information from the user. The system compares the login information to the client database to authenticate the login. If the login does not match a record in the client database, the login page is displayed again for another attempt. If the user subsequently fails to login correctly a predetermined number of times, then the system locks the user's account for a specified time period, or until the account is unlocked by an administrator.

When a login is authenticated, the system displays a patient information and diagnosis page. The user enters patient information and sees a list of diagnoses that are supported in the system databases. The system then receives the diagnosis or diagnoses selected by the user. If more than one diagnosis is selected the system applies an algorithm to merge the order sets and displays a preliminary order set containing all unique orders to the user. The user then has the option to customize the treatment protocol or to print, save, or transmit the order set template. When a user chooses to customize the treatment protocols the system displays a scrollable, context sensitive patient details page. The user scrolls through the page selecting those protocols that are appropriate and entering further information as required. When only a single diagnosis is selected, the system goes directly to this page. After all selections have been made, the system ranks the protocols and displays selected orders while removing unselected items. The system then can receive instructions to send the optimized order set to a printer, to be transmitted electronically, or to a memory storage device.

Figure 3A:
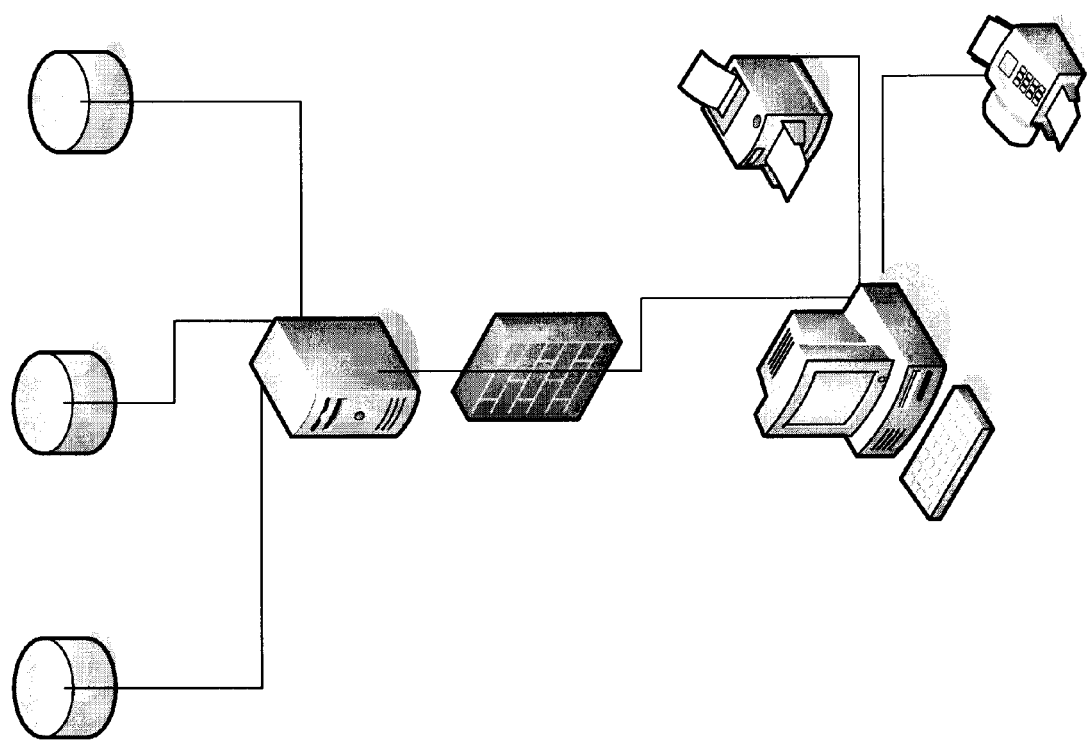
FIG. 3A is a diagram of an embodiment of the system.
Figure 3B:
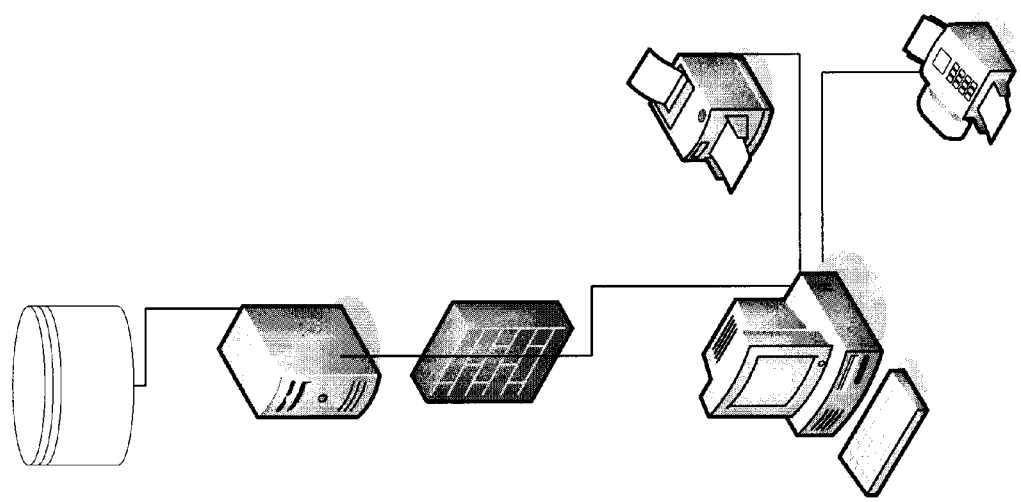
FIG. 3B is a diagram of an embodiment of the system.

Although the entire system can be run from a stand alone computer, in certain embodiments the user interface computer is connected to an application server in a remote location as shown in FIG. 3A or 3B. The server can be connected to the user interface by an intranet, LAN or ETHERNET connection for example, or through an internet connection such as through the world wide web. Although the components in the systems drawn in the figures appear as hardwired, it is understood that any of the components can be connected wirelessly. It is also understood that the server can be connected to a plurality of user interface computers simultaneously and that the users can be within one facility or location or in different facilities or locations.

In embodiments of the disclosure, the application server has access to one or more databases or database collections, stored on computer readable memory, and often contained in one or more database servers, or within a single computer. FIG. 3A is a diagram of a system in which a server is connected to three database containing memory storage devices and FIG. 3B is a diagram of a system in which a server is connected to a single database collection. Three databases or collections that are utilized include a client database or collection that contains the client login information, passwords, users within the client, client specific user roles, client specific display and output parameters and can include special instructions for use by that client. For example, client information can include such items as insurance accepted by that client, use of generics, preference for certain pharmaceuticals or procedures, corporate logos, and other information specific to a client.

A second database or collection, stored on a computer readable memory device is a patient database that can include all the patient records, such as patient name, treating physicians, referring physicians, Medical Record Number, location in the hospital, diet restrictions, allergies, medical history, treatment regimen, patient educational materials, and any other information that would affect treatment of that patient. A third database or collection that is connected to the server is a database of medical best practice protocols organized by diagnosis. It is an aspect of the disclosure that a panel of physicians reviews the medical literature on a regular basis, such as quarterly, and updates the treatment protocols for each diagnosis as appropriate to provide the users the best protocols for each diagnosis using evidence based medical practices.

The systems also include computer readable media containing instructions, or having embedded instructions for providing an interactive display of a list of diagnoses contained in the protocol database or collection, and further provides instructions for receiving the users selections of diagnoses. The diagnoses are grouped by organ system or clinically relevant similarities, and can be arranged in subcategories of specific diagnoses with expandable lists of diagnoses related to that organ, organ system or disease type under a selected heading. Diagnosis groups can include, but are not limited to Abdominal, Pulmonary, Infection, Cardio-Circulatory, Renal, Urinary Tract, Endocrine-Metabolic, Heme-Onc, Neuro-Cerebrovasc, Surgical, Musculoskeletal-Skin, Complications of Tx, or Supplemental Orders. Within each diagnoses list, a user can select one or more, or no diagnoses. In many cases, when selecting a diagnosis, the user is offered more information such as embedded support material for help in making the correct diagnosis and treatment options and for help in selecting the proper industry standard treatment and billing codes.

Once the user has selected a diagnosis, they may either print out all options for treatment regimen, or customize the treatment. Customizing the treatment allows the user to produce an Order Set containing only those treatment protocols deemed appropriate for the treatment.

For a selected diagnosis, the pre-established levels of content hierarchy are examined by computer readable instructions. At each level of hierarchy, unique entities are ranked and displayed based on their display order number. The display order number is designated when the order set template is created by the Order Optimizer administrator.

When multiple diagnoses are selected, software instructions include steps for prioritizing and simplifying the orders, or protocols and medications that can be used to treat each diagnosis. This simplification is accomplished by merging all aspects of the combined diagnoses' Order Sets, and displaying a single Order Set of treatment options, based on the following algorithms:

A. Levels of hierarchy are examined by software instructions. At each level of hierarchy, unique entities are ranked by software instructions and displayed based on their display order number. The display order number is designated when the order set template is created by the Order Optimizer administrator. Within a unique level of hierarchy, constituent aspects of that entity are ranked by software instructions, and displayed according to the following algorithm:
   1. DISPLAY RANK=APPEARANCE COUNT*1000+ USER SELECTION SEQUENCE*100
   2. For items of equal display rank, they are displayed according to the order in which the diagnosis was selected.

Attributes are displayed in descending order based on display rank.
B. The Display Order for each Module is examined; Modules are ranked and displayed based on their Display Order Number. The Display Order Number is designated when the Order Set Template is created.
C. The Display Order of each Modules' components is examined:
1. Item Categories are ranked and displayed based on their Display Order number.
2. The Display Order of each Item Category's Items is examined:
D. Items are ranked and displayed based on their Display Order number.
E. In the event more than one Diagnosis is selected, a unique Order Set is created by merging each Module and its Item Categories according to the following Merging Algorithm:
1. A unique listing of Modules is created, ranked by their respective Display Order.
2. For each unique Module, a unique list of its attributes is created and displayed as follows:
  i. The contents of each Module and its Item Categories are merged. All unique selected items attributes are displayed according to the following formula:
    1. Display Rank=appearance count*1000+user selection sequence*100
    2. For items of equal Display Rank, they are displayed according to the order in which the diagnosis was selected by the user.
  ii. Attributes are displayed in descending order based on Display Rank.

Standard SQL protocols can be used to extract the information from the various databases, or any other appropriate language known in the art can be used.

The software then provides instructions to allow a user to scan through the listed items and select those to appear in the final order set, including all protocols, pharmaceuticals, dosages, tests, therapies, and patient information documents, along with clinical and billing decision support. The instructions include display of a selectable button for "Generate Order Set" on the user's screen. Selection of this button results in a sequence of steps that result in the final order set, including removing all unselected items from the set and generating a final list of orders and attached documentation. This order set can be sent to a printer to receive a hard copy, or it can be sent to by facsimile or by electronic communication as selected by a user.

An aspect of the disclosure is computer readable instructions embedded in a computer readable memory device. The following discussion describes a preferred embodiment of such a structure.

As show in FIG. 2:
(A1) Display Patient Information & Diagnosis Page
The system searches its database, retrieving the parameters to create the page according to the following algorithm:
1. Determine Client Group Clinician is associated with.
2. Retrieve all Diagnosis Organ Group/Clinical Categories names for that Client Group.
  a. (A2) Apply Patient or Client Specific Orders. Search the Database to determine if Customizations exist for a specific entity according to the following algorithm:
    For the highest level of entity hierarchy, examine if a standard or custom hierarchy is associated with that Client Group.
    Having made that determination, proceed to create the display by following steps 3-8.
3. Retrieve all Order Set Template names, Coding Prompts, Additional Clinical Information, and evidence-based medical References for those Organ Group/Clinical Categories.
4. Populate the user interface Diagnosis list with the retrieved Organ Group/Clinical Categories.
5. Populate the user interface Diagnosis list with the retrieved Order Set Template names.
6. When the Clinician selects a Diagnosis, perform the following functions:
  a. place the name of the diagnosis in the Selected Diagnosis window.
    If Additional Clinical Information was retrieved from the database, append a star character "*" to the displayed Diagnosis name.
  b. Place the Coding Prompt associated with the Diagnosis in the Coding Prompt window.
7. If a Clinician highlights a displayed Diagnosis containing Additional information—designated by the "*", and clicks the Show Information button, perform the following function:
  a. Create a new dialog window on the screen.
  b. Place the retrieved Additional Clinical Information in the dialog window.
  c. Display the dialog to the User.
8. If a Clinician highlights a displayed Diagnosis and clicks Reference File, perform the following functions:
  a. Create a new dialog window on the screen.
  b. Place the retrieved Reference File information in the dialog
    If no Reference File exists, place the default No Reference File is Available message in the dialog.

(A3) Merge Order Sets
Levels of hierarchy are examined by software instructions. At each level of hierarchy, unique entities are ranked by software instructions and displayed based on their display order number. The display order number is designated when the order set template is created by the order optimizer administrator.

Within a unique level of hierarchy, constituent aspects of that entity are ranked by software instructions, and displayed according to the following algorithm:
1. DISPLAY RANK=APPEARANCE COUNT*1000+ USER SELECTION SEQUENCE*100
2. FOR ITEMS OF EQUAL DISPLAY RANK, THEY ARE DISPLAYED ACCORDING TO THE ORDER IN WHICH THE DIAGNOSIS WAS SELECTED.
II. ATTRIBUTES ARE DISPLAYED IN DESCENDING ORDER BASED ON DISPLAY RANK.

(A4) Output Order Set Template.
If a Clinician chooses not to customize the treatment protocol, the system outputs the Order Set Template according to the following algorithm:
1. The system retrieves all attributes associated with the Order Set Template. These attributes are represented in the XML programming language as an XML document.
  a. If multiple diagnoses are selected, the system merges all diagnoses into a single, consistent format according to algorithm (A3).
2. The system then takes the XML document, a pre-formatted XSL Style sheet, and inputs both into a $3^{rd}$ party XSLT processor, whose function is to create an intermediate format of the Order Set Template.
3. The XSLT processor outputs the Order Set Template in a formatted, intermediate representation called XSL-FO. This format is used to provide formatting consistency while retaining output flexibility: a single intermediate format—XSL-FO can be further formatted into a variety of user-readable formats, such as PDF, HTML, WML.

4. The XSL-FO document is input into a $3^{rd}$ party Formatting Engine, which outputs the document into the desired user format.

Figure 9:
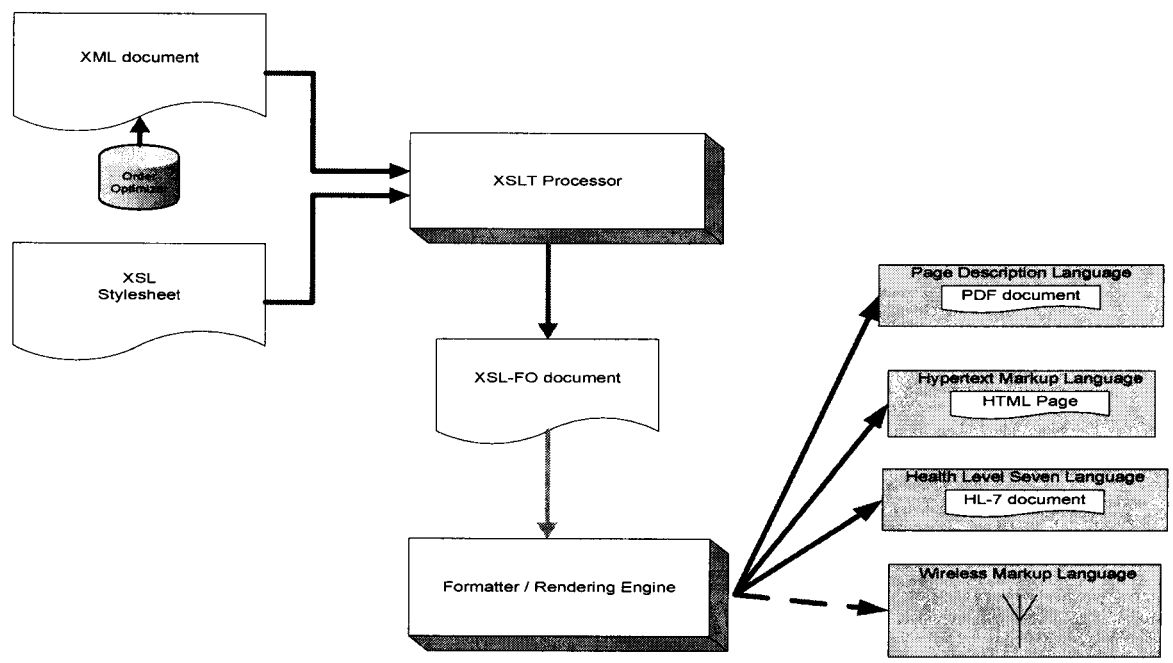
FIG. 9 illustrates the process of creating an end user readable Order Set from data stored within the database(s).

The diagram in FIG. 9 illustrates the process of creating an end user readable Order Set from data stored within the Order Optimizer database.

(A5) Display Scrollable Context Sensitive Patient Details Page.

The system creates a scrollable, interactive, context sensitive page of Patient treatment details according to the following algorithm:

1. The system examines the levels of entity hierarchy for the specified Client Group. The system orders the entities of the highest order of Hierachy according to their Display Order (set by the Administrator.) This Display Order controls in what order the entities of the highest hierarchy will be displayed to the user.
2. Once the system has determined the display order of the highest level hierarchy, the system retrieves the child elements of each entity, according to their Display Order (set by the Administrator.) This Display Order controls in what order the child elements will be displayed to the user.
3. Once the system has determined the display order of child elements, the system retrieves the constituent components of each child element. The constituent components are the descriptive and behavioral characteristics of those components, including text, font, context sensitive behavior. These components will be displayed to the user in the format specified by the Administrator.

(A6) Rank & Display Selected Orders, Remove Unselected Items.

Once the Clinician inputs treatment within the context sensitive page, and clicks the "Generate Order Set Button", the system creates a scrollable, personalized Patient Details Review page of Clinician-input treatment parameters according to the following algorithm:

1. The system examines the completed Order Set Template. Within each highest level of Hierarchy, each child element's constituent components are evaluated as follows:
   a. If the component has been selected by the Clinician, that component is retained for creation the final Order Set (A7).
   b. If the component has not been selected by the Clinician, the system examines the components' behavioral characteristics. If that component has been designated as "Always Print", that component will be retained for the final Order Set (A7).

(A7) Create Paper or Electronic Copy of Order Set.

Once the system has completed algorithm (A6), the retained Order Set is output according to the following algorithm:

1. The system examines the user interface input entries provided by the Clinician.
2. The system retains all attributes designated by the Clinician.
3. The system formats the Order Set output per algorithm (A4), steps 1a-4.

Figure 4:
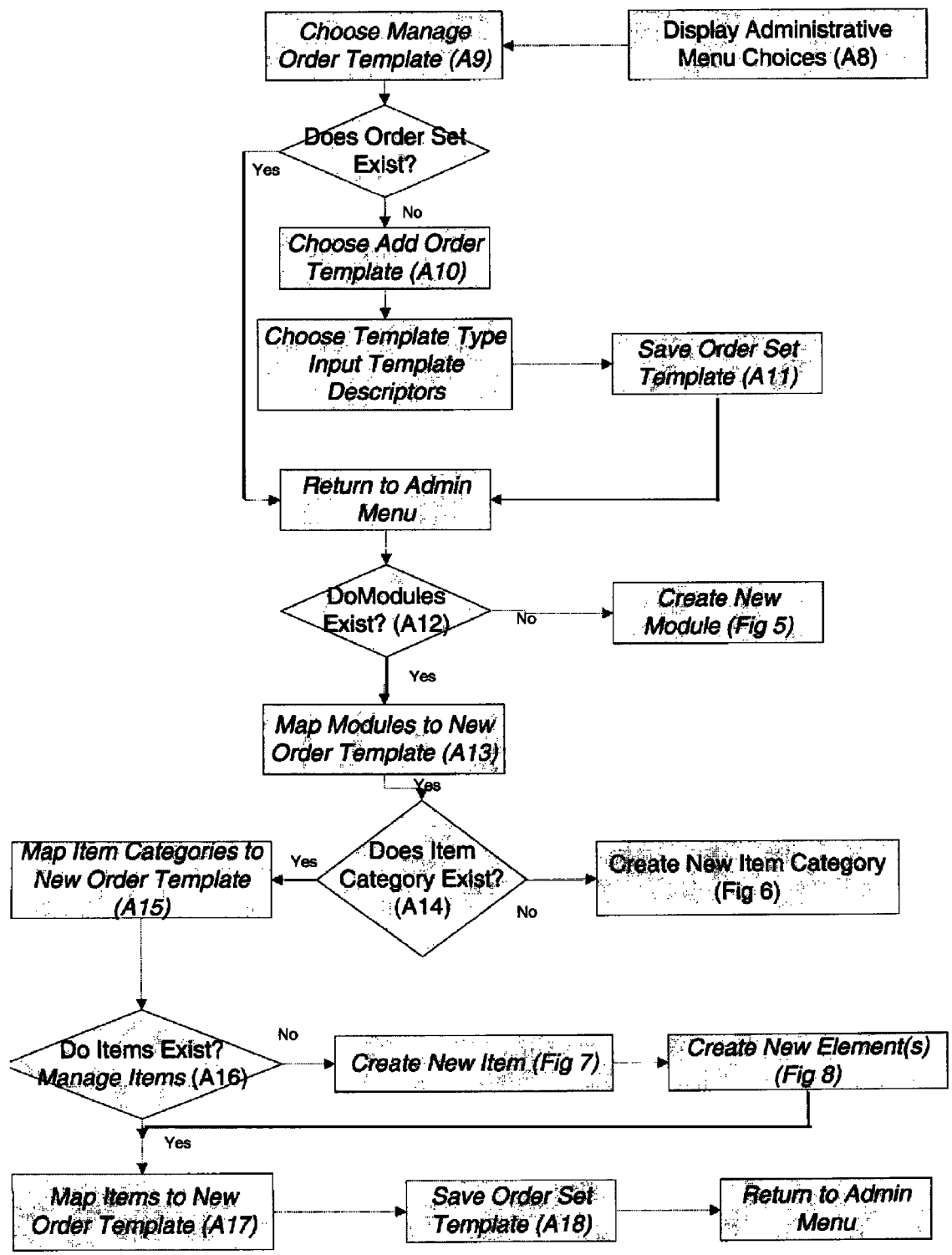
FIG. 4 is a diagram of an administrative system to create a new order set template.

It is a further aspect of the disclosure that the computer readable instructions include the ability to create additional items and to build them into the system for use in creating order sets. This aspect is illustrated in FIG. 4.

(A8) Display Administrative Menu Choices.

From the Main Menu, the Administrator selects the "Admin" menu choice on the left hand page. The system searches the database according to the following algorithm:

1. For the system menu of Admin, retrieve all Admin menu item descriptions, and menu item id's.
2. Display the retrieved menu item descriptions in a list of hyperlinks immediately under the Admin menu choice. This list can be expanded or contracted by clicking on a visual element on the screen adjacent to the Admin label. Clicking on any hyperlink would cause the system to display that choice to the user.
3. Additionally, display the retrieved item descriptions in a list of hyperlinks within a table in the center of the screen. Clicking on any hyperlink would cause the system to display that choice to the user.

(A9) Manage Order Template.

From the Admin Menu, the Administrator can choose to create or modify a diagnosis Order Set Template by clicking on the Manage Order Template. The system searches the database according to the following algorithm:

1. For the Client Group selected by the Administrator upon login, retrieve all existing Order Set Templates. Display a list of those templates in a table in the center of the screen, one per row. Each template row would list the Order Set Template's Template Name, Template Type, and Template Description. The Template Name would be displayed as hyperlinked text, allowing the user to retrieve, view, and edit the Order Template's details (A10).

(A10) Choose Add Order Template.

From the Manage Order Template screen (A9), the user can add or edit an Order Template. If the desired diagnosis Order Template is not listed on the Manage Order Template screen, the Administrator can add one by clicking on the "Add Order Template" button. The system performs the following actions:

1. Searches the database of a list of all existing Template Types, and displays them in a drop-down list on the screen.
2. Displays a text entry area allowing the user to enter the Template Name. This name will be displayed to Administrators when they use the system. Clinician users will see this Template Name when selecting a diagnosis from the Patient Details screen (A1). Administrators will see this template name when selecting Manage Order Templates. (A9).
3. Displays a text entry area allowing the Administrator to enter the Template Description. Administrators will see this Template Description when selecting Manage Order Templates. (A9).

(A11) Save Order Set Template.

Once an Administrator has input or edited a Template Type, Template Name, and Template Description (A10), the Administrator clicks "Save". This causes the system to perform the following actions:

1. Store the Order Template in the database table, assigning it a unique ID.
2. Associate this newly stored Order Template with the Client Group by entering its ID in that table.

(A12) Do Modules Exist?

The Administrator selects the "Manage Modules" hyperlink from the Admin Menu at the left side of the screen. The system displays all existing modules for that Client Group according to the following algorithm:

1. For the Client Group selected by the Administrator upon login, retrieve all existing Order Set Modules. Display a list of those Modules in a table in the center of the screen, one per row. Each Module row would list the Modules' Name and Description. The Module Name would be displayed as hyperlinked text, allowing the user to retrieve, view, and edit the Module's details (A19).

(A13) Map Modules to New Order Set Templates

Once the Administrator has created a new Order Set Template (A10) (A11), and determined that the desired Modules already exist within the system (A12), the Administrator must associate the existing Modules to the new Order Set Template. This process—called Map Modules—is accomplished according to the following algorithm:

1. The Administrator clicks the "Map Module" button on the Manage Modules screen.
2. The system displays a new screen to the User, entitled Map Modules.
3. The Administrator selects the new Order Set Template created by (A10) (A11) from a drop down list, and clicks the "Apply Filter" button.
4. The system searches the database, retrieving all existing Modules available to be associated with the Order Template and displaying them in a window entitled "Available." Modules already assigned to the Order Set Template are displayed in the "Assigned" window.
5. The Administrator assigns desired Modules to the new Order Set Template using the "Add", "Add All", "Remove", "Remove All" buttons. Clicking Add or Add All moves those Modules to the Assigned window. Clicking "Remove" or "Remove All" moves those Modules from the Assigned window to the Available Window.
6. The Administrator manipulates the order in which Modules appear within the Order Set Template by highlighting the Module in the Assigned window, and clicking "Move Up" or "Move Down."
   a. The Move Up and Move Down buttons cause the system to create a Display Order value for that Module in the database, associated with ONLY that specific Order Set.
7. The Administrator saves the Modules associated with the Order Set Template by clicking "Save".
   a. The system inserts/updates the database, saving a record of the Modules, their Display Order, and the Order Set Template, and associating that record with the Client Group designated by the Administrator upon login.

(A14) Does Item Category Exist?

The Administrator selects the "Manage Item Categories" hyperlink from the Admin Menu at the left side of the screen. The system displays a new screen to the User, entitled Manage Item Categories.

1. The Administrator selects the Module—either an existing Module or one created by (A12) (A13) from a drop down list, and clicks the "Apply Filter" button.
2. The system searches the database, retrieving all existing Item Categories associated with the Module, and displaying them in a window entitled "Manage Item Categories." The Window displays a list of those Item Categories in a table in the center of the screen, one per row. Each Item Category row would list the Item Category's Name and Description. The Item Category Name would be displayed as hyperlinked text, allowing the user to retrieve, view, and edit the Item Category's details (A15) (A20).

(A15) Map Item Categories to New Order Template.

Once the Administrator has created a new Module (A12) (A13), and determined that the desired Item Categories already exist within the system (A14), the Administrator must associate the existing Item Categories to the new Module. This process—called Map Item Category—is accomplished according to the following algorithm:

8. The Administrator clicks the "Map Item Category" button on the Manage Item Category screen.
9. The system displays a new screen to the User, entitled Map Item Category.
10. The Administrator selects the new Order Set Template and Module created by (A10) (A11) (A12) (A13) from a drop down list, and clicks the "Apply Filter" button.
11. The system searches the database, retrieving all existing Item Categories available to be associated with the Order Template & Module, and displays them in a window entitled "Available." Item Categories already assigned to the Order Set Template & Module are displayed in the "Assigned" window.
12. The Administrator assigns desired Item Categories to the new Order Set Template & Module using the "Add", "Add All", "Remove", "Remove All" buttons. Clicking Add or Add All moves those Item Categories to the Assigned window. Clicking "Remove" or "Remove All" moves those Item Categories from the Assigned window to the Available Window.
13. The Administrator manipulates the order in which Item Categories appear within the Order Set Template Module by highlighting the Item Category in the Assigned window, and clicking "Move Up" or "Move Down."
    a. The Move Up and Move Down buttons cause the system to create a Display Order value for that Item Category in the database, associated with ONLY that specific Order Set & Module.
14. The Administrator saves the Item Categories associated with the Order Set Template's Module by clicking "Save".
    a. The system inserts/updates the database, saving a record of the Item Categories, their Display Order, and the Order Set Template & Module, and associating that record with the Client Group designated by the Administrator upon login.

(A16) Manage Items

The Administrator selects the "Manage Items" hyperlink from the Admin Menu at the left side of the screen. The system displays a new screen to the User, entitled Manage Items.

1. The Administrator selects the Module—either an existing Module or one created by (A12) (A13) from a drop down list, and also selects the Item Category—either an existing Module or one created by (A14) (A15) from a drop down list and clicks the "Apply Filter" button.
2. The system searches the database, retrieving all existing Item Categories associated with the Module, and displaying them in a window entitled "Manage Item Categories." The Window displays a list of those Item Categories in a table in the center of the screen, one per row. Each Item Category row would list the Item Category's Name, & Description. The Item Category Name would be displayed as hyperlinked text, allowing the user to retrieve, view, and edit the Item Category's details (A15) (A20).

(A17) Map Items to New Order Template

Once the Administrator has created a new Module (A12) (A13), and determined that the desired Item Categories already exist within the system (A14), and associated the existing Item Categories to the new Module (A16), existing Items must be associated with the Item Category, or new ones Created (A22) (A23). This process—called Map Items—is accomplished according to the following algorithm:

1. The Administrator clicks the "Map Items" button on the Manage Items screen.
2. The system displays a new screen to the User, entitled Map Items.
3. The Administrator selects the Order Set Template, Module, and Item Category created by (A10) (A11) (A12) (A13) (A14) (A15) from a drop down list, and clicks the "Apply Filter" button.
4. The system searches the database, retrieving all existing Items available to be associated with the Order Template, Module, and Item Category combination, and displays them in a window entitled "Available." Items already assigned to the Order Template, Module, and Item Category combination are displayed in the "Assigned" window.
5. The Administrator assigns desired Items to the new Order Template, Module, and Item Category combination using the "Add", "Add All", "Remove", "Remove All" buttons. Clicking Add or Add All moves those Items to the Assigned window. Clicking "Remove" or "Remove All" moves those Items from the Assigned window to the Available Window.
6. The Administrator manipulates the order in which Items appear within the Order Set Template Module's Item Category by highlighting the Item in the Assigned window, and clicking "Move Up" or "Move Down."
   a. The Move Up and Move Down buttons cause the system to create a Display Order value for that Item in the database, associated with ONLY that specific Order Template, Module, and Item Category combination.

(A18) Save Order Set Template

The Administrator saves the Order Set Template, and the Items associated with the Order Set Template Modules' Item Category Module by clicking "Save".
   a. The system inserts/updates the database, saving a record of the Items, their Display Order, and the Order Template, Module, and Item Category combination, and associating that record with the Client Group designated by the Administrator upon login.

(A19) Manage Modules

Figure 5:
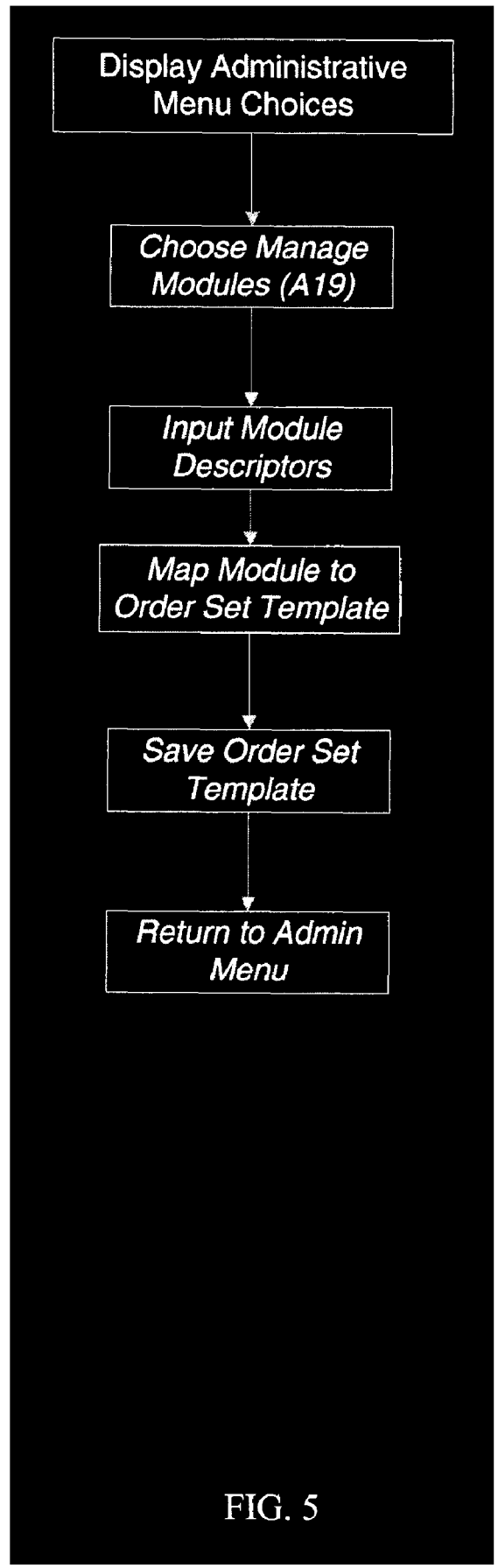
FIG. 5 demonstrates the instructions for managing modules in order set generation by an administrator.

The diagram in FIG. 5 demonstrates the instructions for managing modules by an administrator. From the Admin Menu, the Administrator can choose to create or modify a Module by clicking on the Manage Modules hyperlink. The system searches the database according to the following algorithm:
   1. For the Client Group selected by the Administrator upon login, retrieve all existing Modules. Display a list of those Modules in a table in the center of the screen, one per row. Each Module row would list the Module's Module Name, Module Description. The Module Name would be displayed as hyperlinked text, allowing the user to retrieve, view, and edit the Module's details (A13).

(A20) Manage Item Categories

Figure 6:
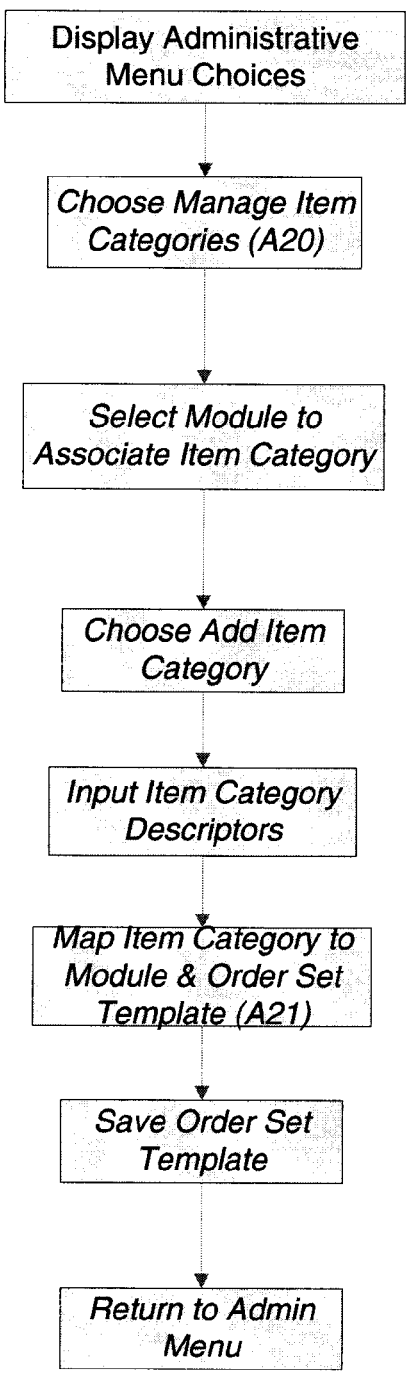
FIG. 6 demonstrates the steps in managing item categories by an administrator.

The steps in managing item categories is shown in the diagram in FIG. 6. From the Admin Menu, the Administrator can choose to create or modify a Module by clicking on the Manage Modules hyperlink. The system searches the database according to the following algorithm:
   1. For the Client Group selected by the Administrator upon login, retrieve all existing Modules. Display a list of those Modules in a table in the center of the screen, one per row. Each Module row would list the Module's Module Name, Module Description. The Module Name would be displayed as hyperlinked text, allowing the user to retrieve, view, and edit the Module's details (A13).

(A21) Create Item Category

Once the Administrator has searched existing Item Categories and determined that the desired one does not exist (A14), the Administrator can create a new one. If the desired Item Category is not listed on the Manage Item Categories screen, the Administrator can add one by clicking on the "Add Order Template" button. The system performs the following actions:
   1. Displays a drop down list to select the Module to which to associate the new Item Category
   2. Displays a text entry area allowing the user to enter the Item Category Name. This name will be displayed to all Administrators when they use the system.
   3. Displays a drop down list to select descriptive and behavioral attributes such as font style and behavior when creating output
   4. Displays a text entry area allowing the Administrator to enter the Item Category Description. Administrators will see this Description when selecting Manage Item Categories. (A14).

(A22) Save Item

Figure 7:
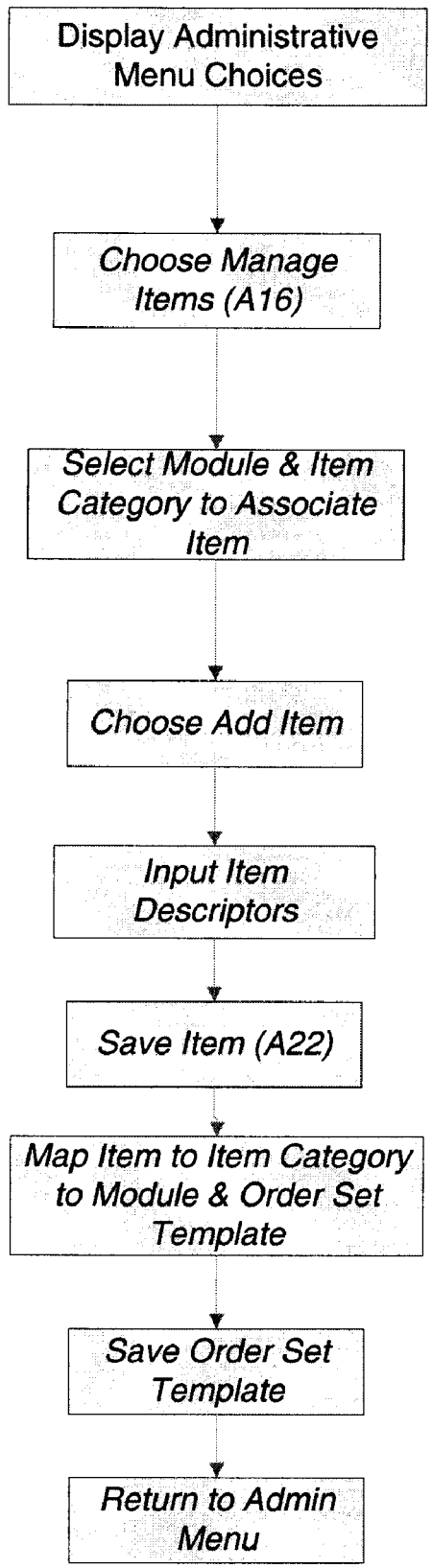
FIG. 7 is a diagram of steps performed to manage items and to map them to item categories, modules, order set template.

The steps in creating items is shown in FIG. 7. The Administrator saves the Item, and the Item Category and Module associated with the Order Set Template, by clicking "Save".
   1. The system inserts/updates the database, saving a record of the Item, their Elements and Display Order, and the Order Template, Module, and Item Category combination, and associating that record with the Client Group designated by the Administrator upon login.

(A23) Add Element

Figure 8:
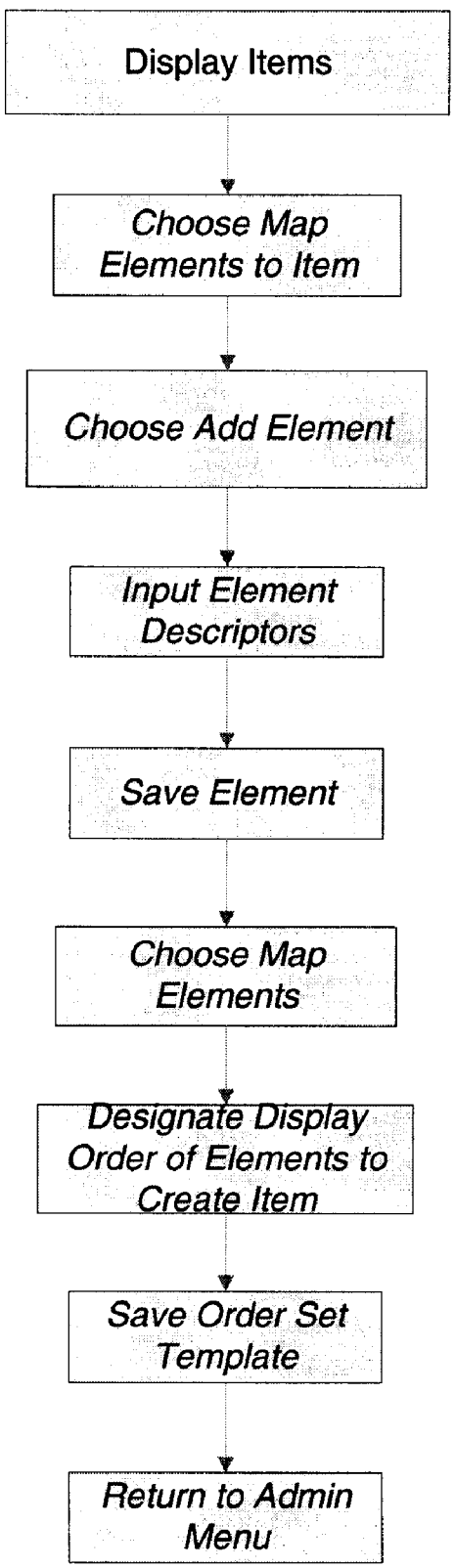
FIG. 8 is a diagram of steps in mapping elements to items.

Elements are the building blocks of Items. An Element could be a single letter, word, or punctuation mark. As such, the Administrator creates an Item after having determined that no suitable item exists. Steps for creating items are shown in FIG. 8. To create an Item, the Administrator selects Manage Items (A16), inspects the Item names for suitable Items, and then clicks the Hyperlink "Map Elements to Item" if it is determined that no suitable item exists. The system performs the following actions:
   1. Displays a new screen, entitled Add/Edit Element.
   2. Displays a text area to enter Element Name. This name is used for taxonomy purposes, and to allow an Administrator to recognize the element as a reusable component. For example, when creating a Period element for punctuation, the Element Name might be entitled Punctuation Period Character.
   3. Displays a text area to enter Display. This field is used to capture the actual value of the Element. For example, when creating a Period element for punctuation, the Display might be "."
   4. Display a drop down list to select the formatting Style Name to which to output the new Element.
   5. Display a drop down list to select the formatting Control Type—for example a Checkbox—to which to output the new Element.
   6. Display a drop down list to select the formatting Element Type—for example Hide While Printing—to which to govern the Element's behavior upon output.
   7. Displays a text area to enter Element Width. This field is used to format the Element on Output.
   8. Displays a text area to enter Element Height. This field is used to format the Element on Output.

(A24) Save Element

The Administrator saves the Element by clicking "Save".

1. The system inserts/updates the database, saving a record of the Element, its Item, Item Category, Module, and Order Set Template and associating that record with the Client Group designated by the Administrator upon login.

(A25) Map Elements

Once the Administrator has created a new Element (A24) (A25), the new Elements—as well as existing ones desired to be reused—must be aggregated. This process—called Map Elements—is accomplished according to the following algorithm:

1. The Administrator clicks the "Map Elements" button on the Manage Elements screen.
2. The system displays a new screen to the User, entitled Map Elements.
3. The system searches the database, retrieving all existing Elements available to be associated with the Order Template, Module, Item Category, and Item combination, and displaying them in a window entitled "Available." Items already assigned to the Order Template, Module, Item Category, Item combination are displayed in the "Assigned" window.
4. The Administrator assigns desired Items to the new Order Template, Module, Item Category, Item combination using the "Add", "Add All", "Remove", "Remove All" buttons. Clicking Add or Add All moves those Elements to the Assigned window. Clicking "Remove" or "Remove All" moves those Elements from the Assigned window to the Available Window.
5. The Administrator manipulates the order in which Elements appear/aggregate by highlighting the Element in the Assigned window, and clicking "Move Up" or "Move Down."
   a. The Move Up and Move Down buttons cause the system to create a Display Order value for that Element in the database, associated with ONLY that specific Order Template, Module, Item Category, Item combination.

The present disclosure can be described, therefore in certain embodiments as computer readable media with embedded instructions for receiving patient information from the user interface and for sending or retrieving information about a patient to or from the patient information database; computer readable media with embedded instructions for receiving a request to display a list of diagnoses to the user interface upon receipt of a request for diagnoses from the user interface; computer readable media with embedded instructions for receiving selections of one or more diagnoses from the user interface, for retrieving protocols for the selected one or more diagnoses from the current protocol database, prioritizing the orders within the set of selected diagnoses such that the orders are ranked by number of occurrences within the set of selected diagnoses and by order of selection of diagnosis, and wherein repeated orders are removed, modifying orders within the set based on client specific information retrieved from the client database, and transmitting the prioritized unique orders to the user interface; and computer readable media with embedded instructions for receiving selections and modifications of orders from the user interface, removing non-selected orders, and transmitting an order set to the user interface.

It is understood that the disclosed systems can include a server connected to a user interface by various means known in the art, including, but not limited to an intranet or internet connection, either wireless or hardwired, or the system can be contained in a stand alone computer.

The present disclosure can also be described in certain embodiments as a computerized system for providing medical orders for a patient, wherein the system comprises:

an application server connectable to an interactive user interface, and to one or more computer readable memory storage devices comprising one or more databases for storing client information, patient information, and medical protocol information, the application server comprising a computer readable memory media comprising embedded information comprising;

means for receiving patient information from the user interface and for sending or retrieving information about a patient to or from a patient information database;

means for receiving user selections of one or more diagnoses for a patient, and providing a medical order set to the user based on the selected diagnoses, wherein the order set includes protocols prioritizing the orders within the set of selected diagnoses such that the orders are ranked by number of occurrences within the set of selected diagnoses and by order of selection of diagnosis, and wherein repeated orders are removed, modifying orders within the set based on client specific information retrieved from the client database, and transmitting the prioritized unique orders to the user interface; and means for receiving selections and modifications of orders from the user interface, removing non-selected orders, and transmitting an order set to the user interface.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Figure 10:
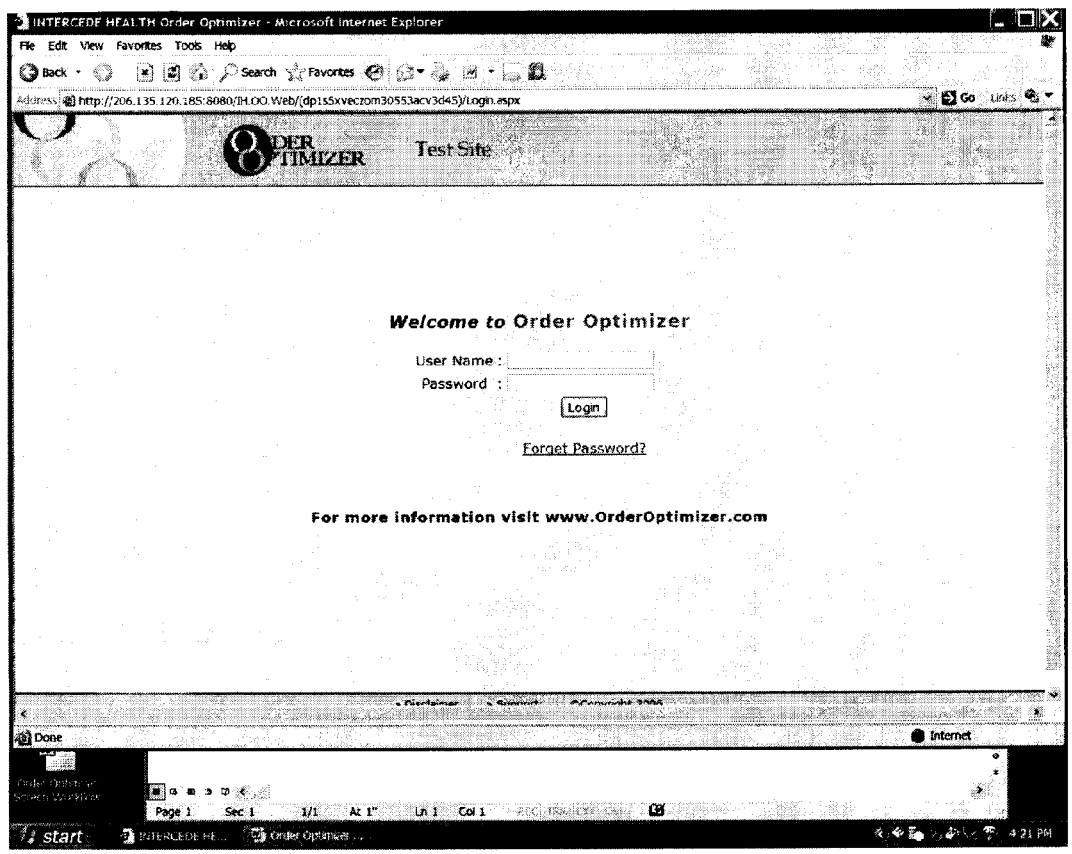
FIGS. 10-17 are screen shots of an example of a user interface display as disclosed herein.

FIGS. 10-17 are screen shots of an example of a user interface as disclosed herein. FIG. 10 is an example of a user login page. Entering a correct username directs the software to access the user database and compare the entered password to the password stored for that user name. A correct username and password allows the user to enter the system. The accessed user database also can contain user specific elements and/or modules that have been created by an administrator such as users within the client, client specific user roles, client specific display and output parameters and can include special instructions for use by that client, such as insurance accepted by that client, use of generics, preference for certain pharmaceuticals or procedures, and corporate logos, for example.

Figure 11:
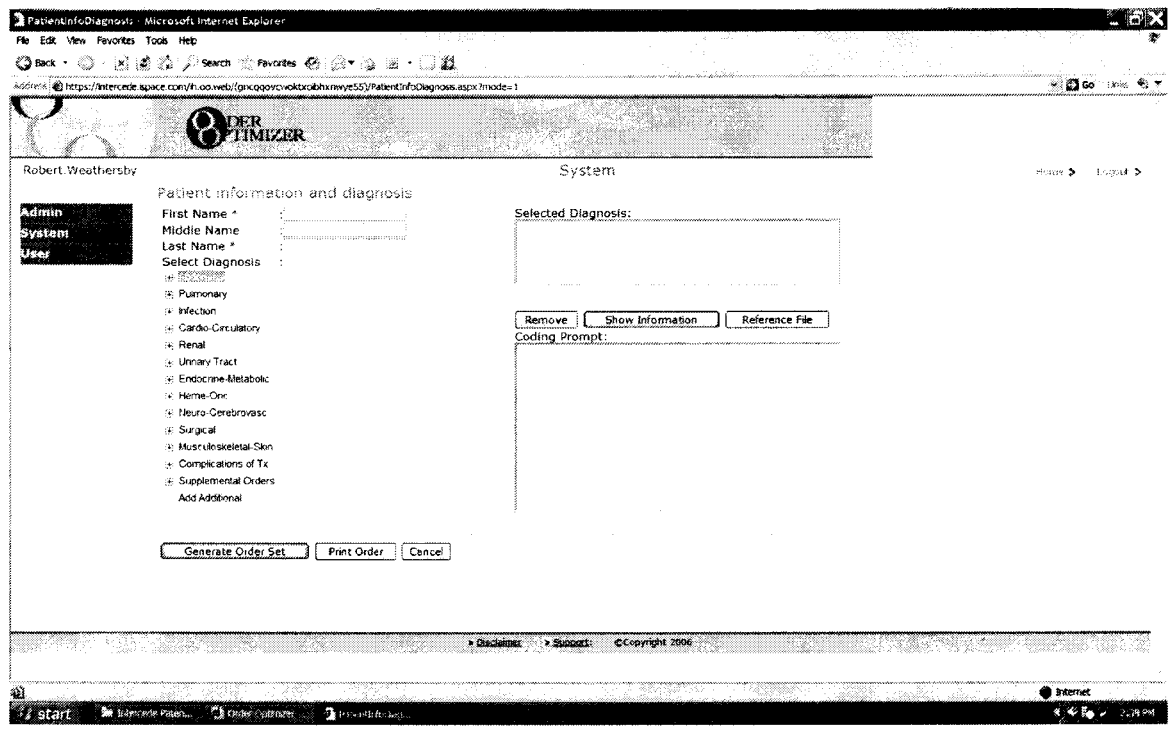
Figure 12:
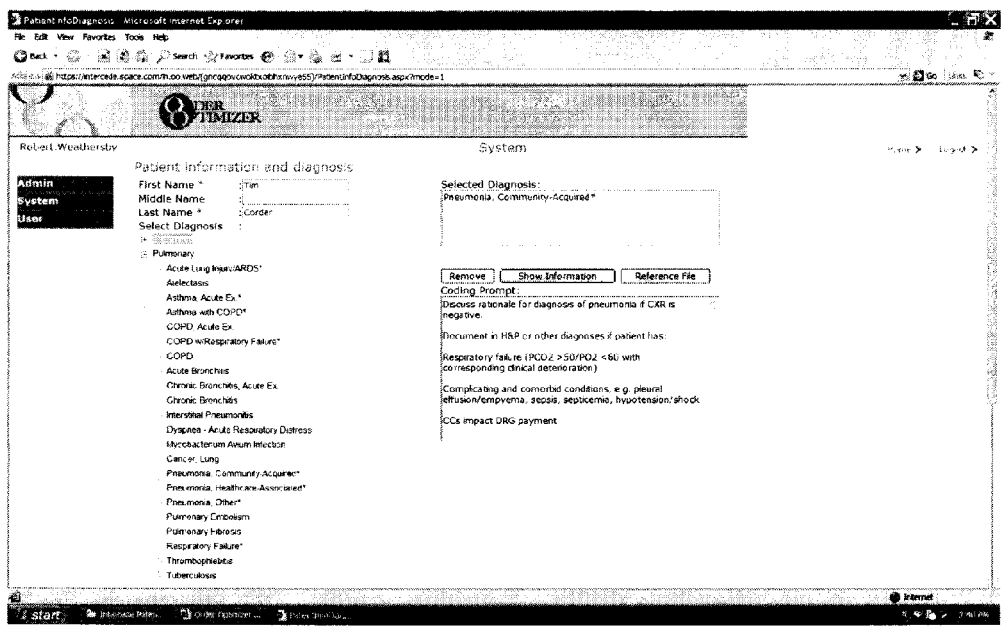
Figure 13:
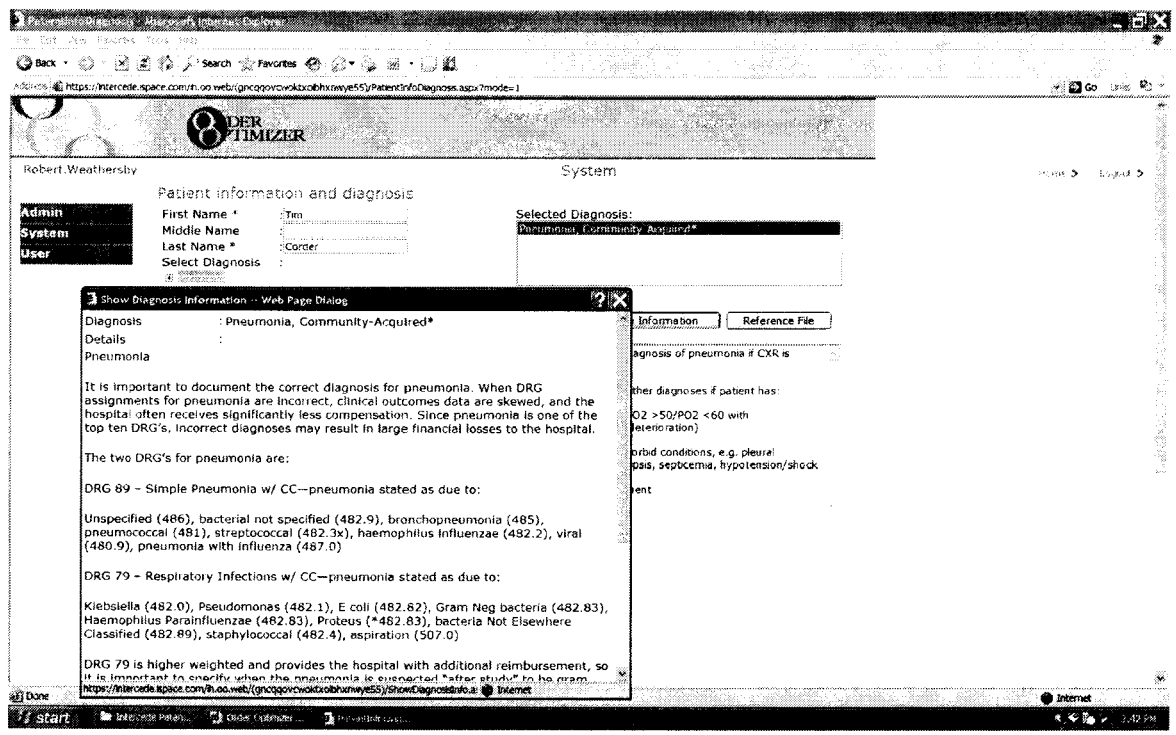

After a successful login, the software can display a patient information and diagnosis page on the user interface as shown in FIG. 11. On this page, a user enters the patient name in the appropriate boxes. As shown in FIG. 11, the user interface displays a list of diagnoses in the database, organized under expandable headings of organ systems or clinically relevant groups of diagnoses. The user selects one or more diagnoses in the order of most relevant to least relevant by pointing and mouse clicking, by keyboard strokes, voice commands or other selection methods, and the selected diagnoses are displayed in the box to the right titled "Selected Diagnosis:" and a coding prompt, if available is shown in the lower box, labeled "Coding Prompt:" as shown in FIG. 12. After the diagnoses are displayed, the user can rearrange them to place them in the correct descending order in the box. A selection button is provided to remove any previously selected diagnosis. Additionally, those diagnoses for which further information is provided are indicated by an asterisk (*) or other symbol. Selecting "Show Information" for a selected diagnosis results in a dialog box containing diagnosis information for the selected diagnosis as shown in FIG. 13. The information includes, but is not limited to diagnosis and treatment decision support materials and/or billing code information. The Clinician can also view the evidence based medical references upon which the diagnosis regimen is based.

Figure 14:
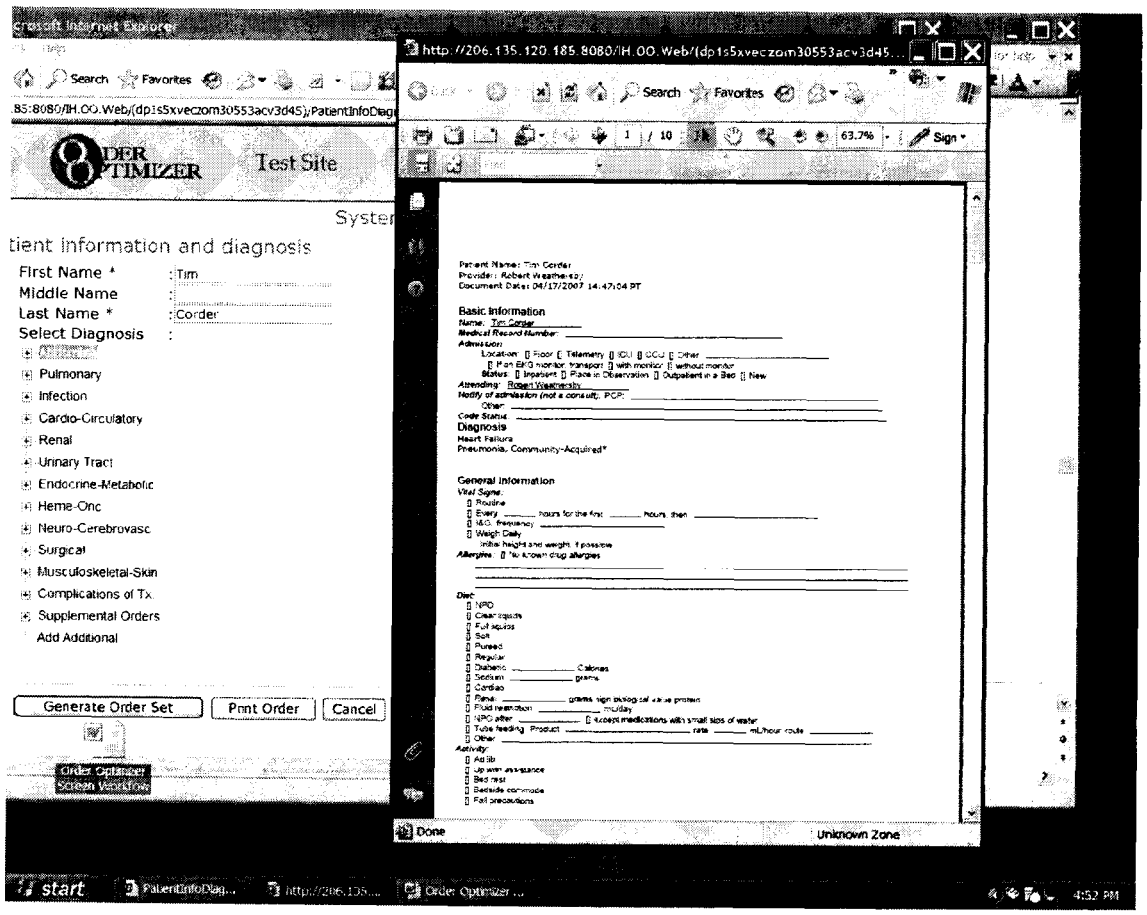

After selecting all appropriate diagnoses, the user can select to print order by a button provided on the user interface or by other user input device. The print order command generates a blank order as shown in FIG. 14. This blank order is generated using an algorithm that filters and prioritizes the items in the order set as described herein. Only unique orders or directives are included, and the directives are listed from highest to lowest display order number as assigned by the ranking algorithms. The user can then fill in this order set by hand if she so chooses.

Figure 15:
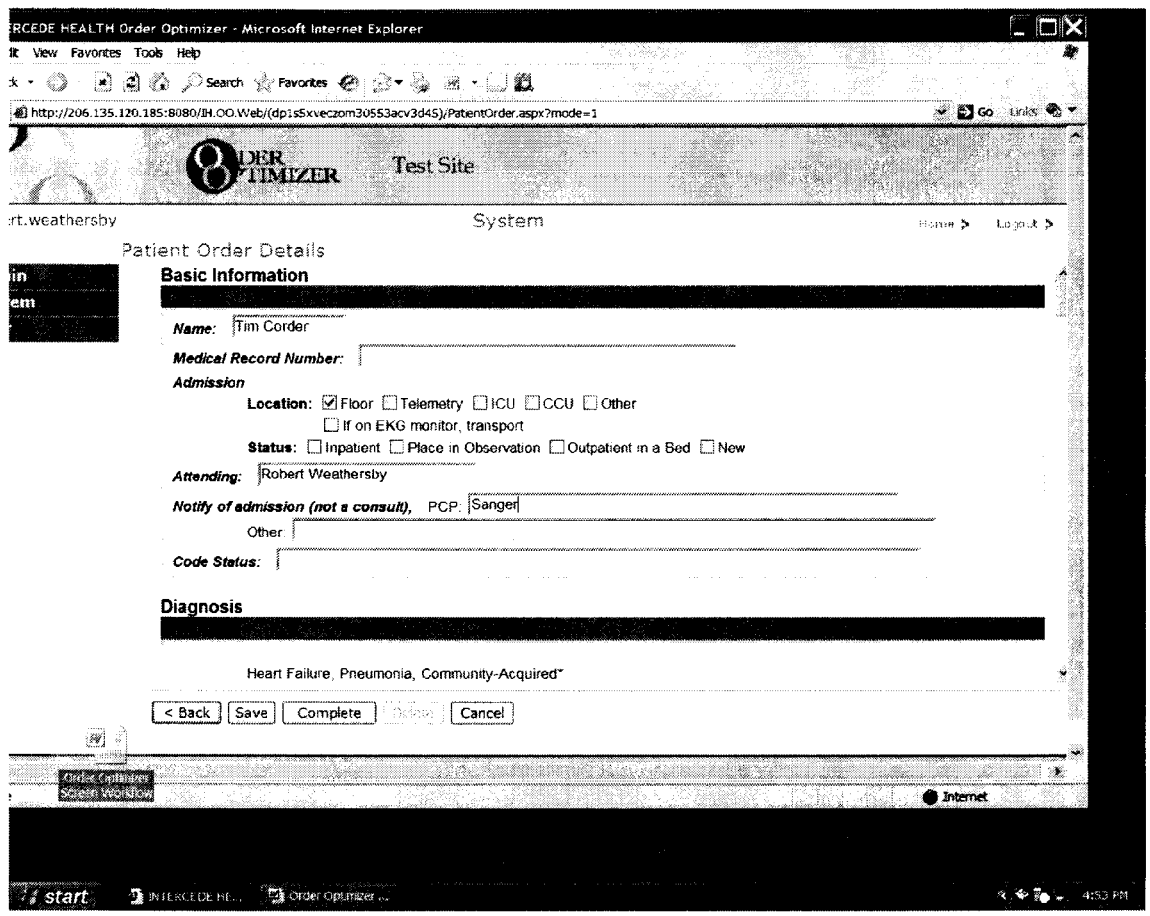

Alternatively, the user can select the provided Generate Order Set command, which generates a scrollable, context sensitive Patient Details page that has been filtered and prioritized, with decision support built in and invoked as choices are made. As shown in FIG. 15, the Basic Patient Information includes stored in the patient information database, and further information can be added by the user. Typical information can include, patient name, medical record number, admission (in a hospital setting), status, attending physician, physician to notify, code status, and other information. The selected diagnosis or diagnoses are also displayed.

Figure 16:
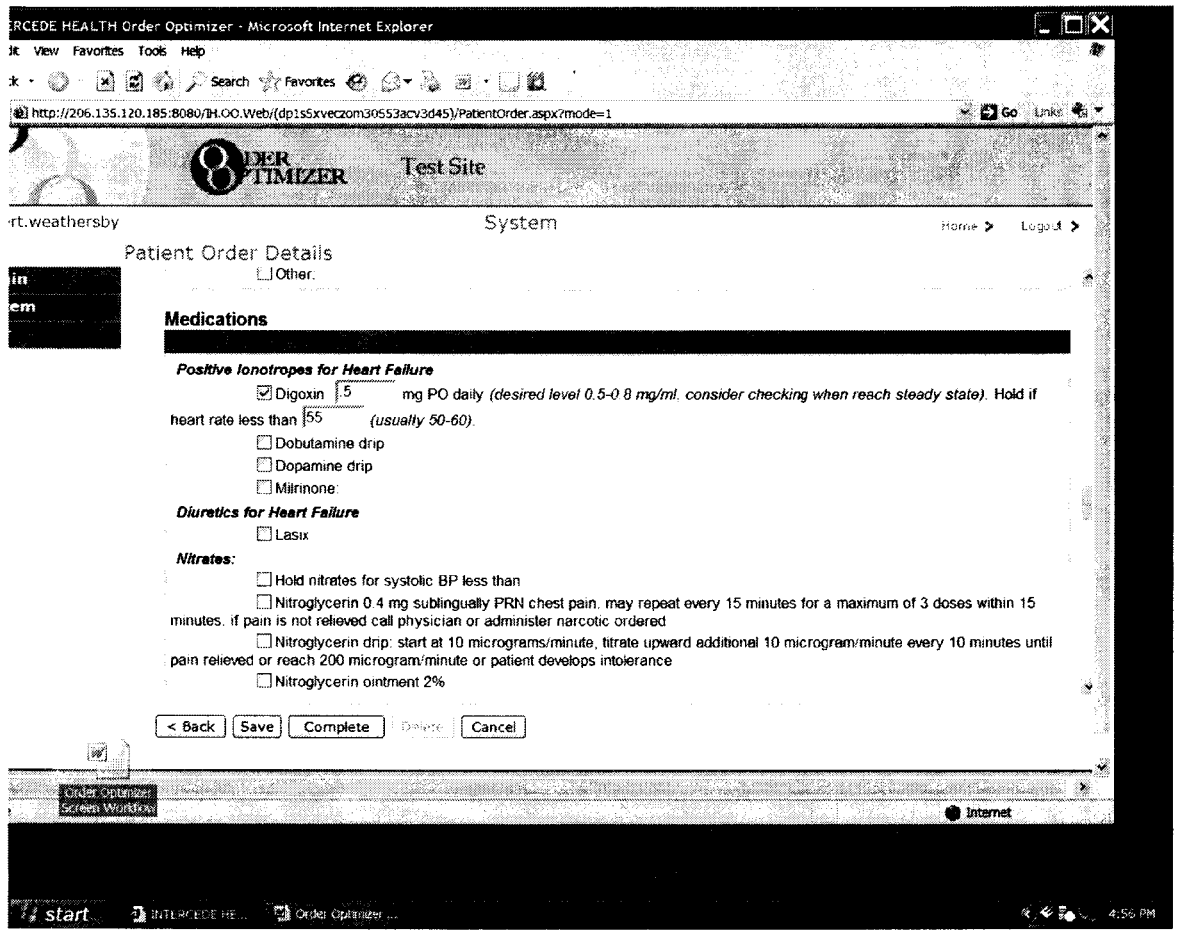

Directives for the order set are displayed on the user interface in categories such as medications as shown in FIG. 16, for example. Other categories can include, but are not limited to Basic Information, Diagnosis, General Information, Laboratory Studies, Diagnostic Studies, or Medications. In the example shown in FIG. 16, for a diagnosis of heart failure, a list of unique directives are shown. In some cases the directives include decision support materials. For example, selecting Digoxin as shown for "Positive Ionotropes for Heart Failure" toggles on the support material following the check box. If the box is not checked by the user, then this material does not show up on the interface.

Figure 17:
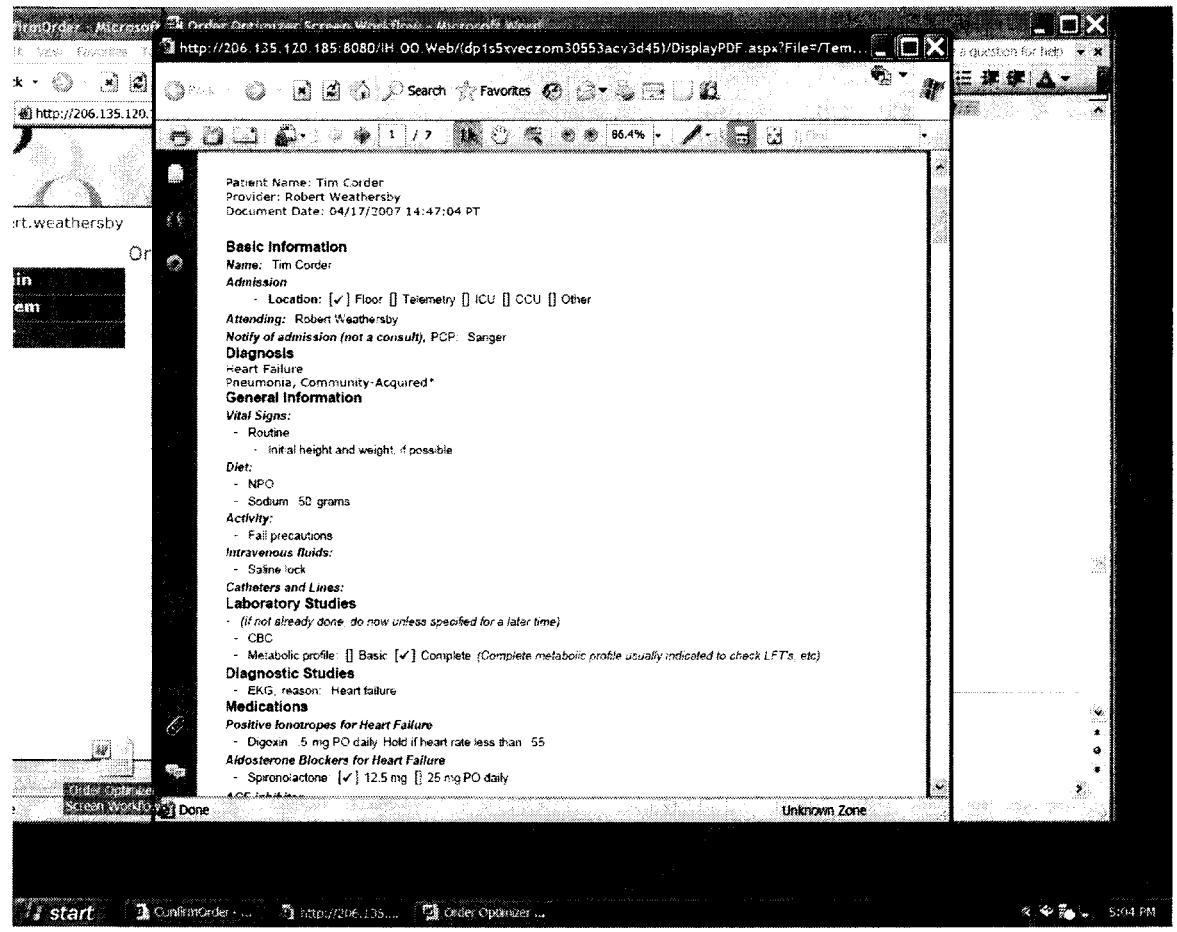

When the user has completed the Order entry, clicking the Complete button generates an optimized Order Set for review. In optimizing an order set, an algorithm filters the Order Set and removes any non-selected directives. Only items that are selected or input by the user are displayed. The user can then choose any combination of printing the Order Set, saving it on a memory device, or transmitting the Order Set electronically, preferably using a healthcare industry standard format. An example of an optimized Order Set is shown in FIG. 17.

EXAMPLE 2

Figure 18:
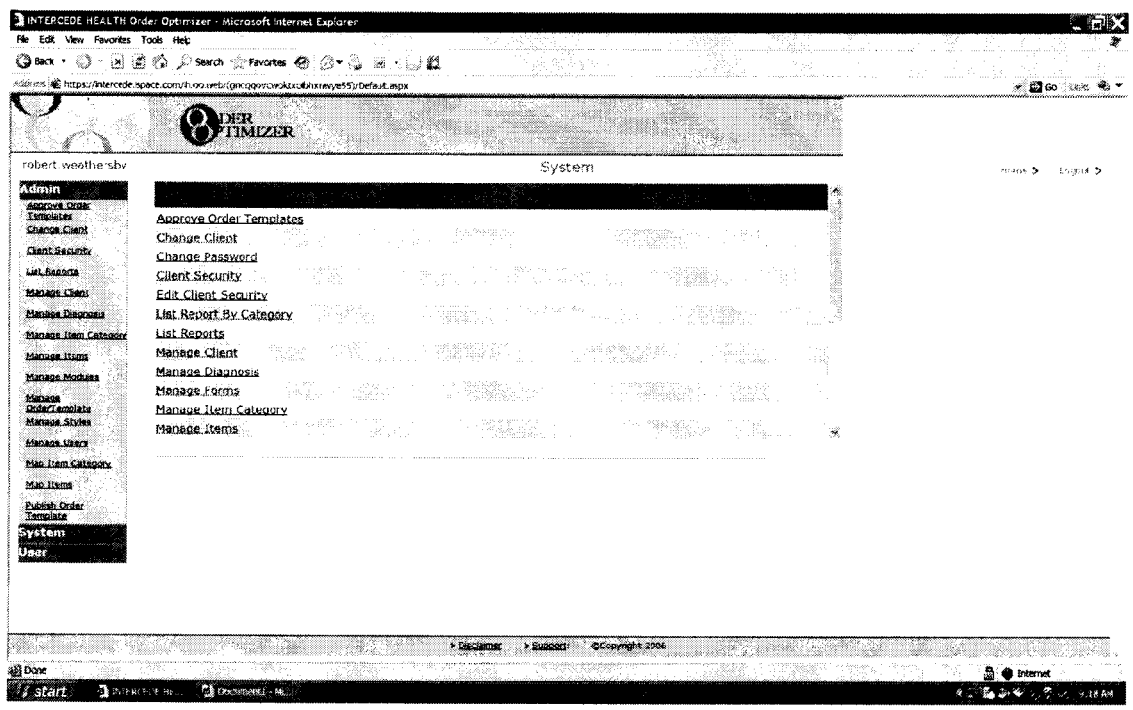
FIGS. 18-39 are screen shots of an example of the use of the disclosed systems and methods in building a system for providing an optimized order set as described herein.

FIGS. 18-37 are screen shots of an example of the use of the disclosed systems and methods in building a system for providing an optimized order set as described herein. Order Set Templates are created and maintained by the Order Optimizer Administrator. The Administrator logs in to the system, and chooses "Admin" from the menu choices on the left hand of the screen as shown in FIG. 18. The present example demonstrates an embodiment including building a new diagnosis capability. The administrator chooses "Manage Diagnosis" from the list of available options.

Figure 19:
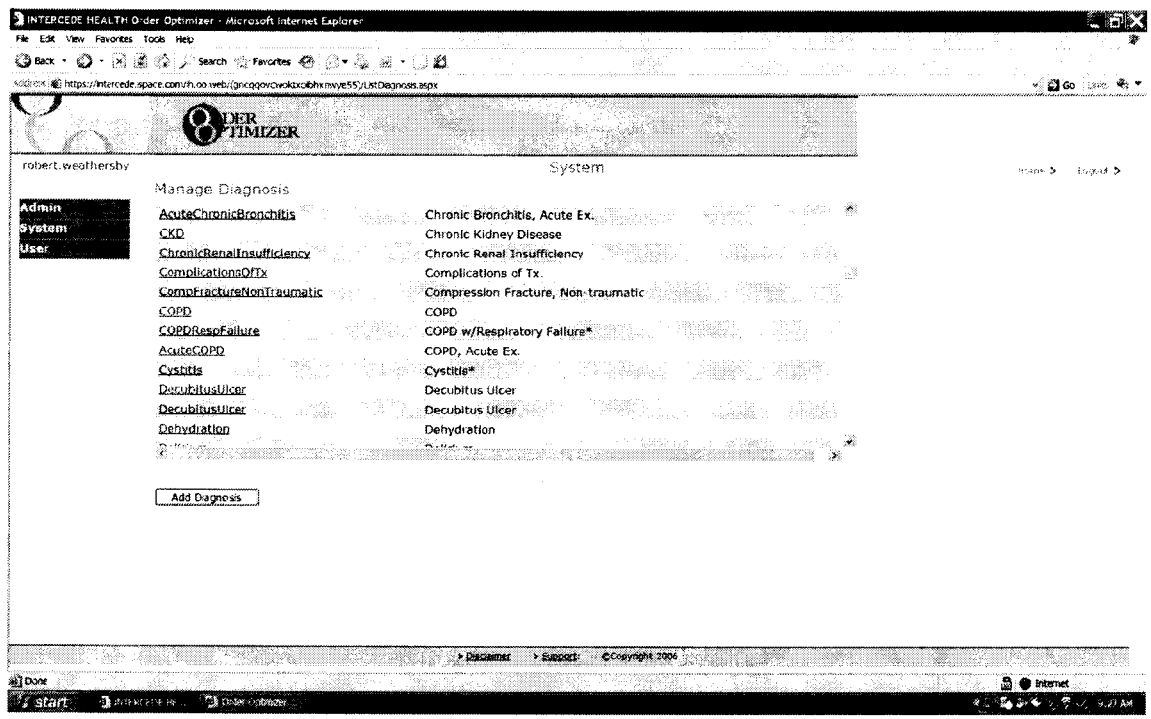

To create a new diagnosis Order Set, after the Administrator chooses Manage Diagnosis from the Admin Menu, he is presented with a screen containing all existing diagnosis Order Set templates, as shown in FIG. 19. In this example, the Admin will create an Order Set for a diagnosis of Depression. Since "Depression" is not in the current list of diagnoses, the Admin selects "Add Diagnosis." This selection directs the software to display the screen shown in FIG. 20, the Add/Edit diagnosis screen. The Admin enters values for Diagnosis name, clinical hierarchy, clinical decision support Prompts, Additional Information (if any), and supplemental document names (if any). Clicking "Save" saves the new Order Set template in this example "Depression", in the diagnosis database. The next steps are to create the Modules, Item Categories and Elements of the new Order Set for Depression.

Figure 20:
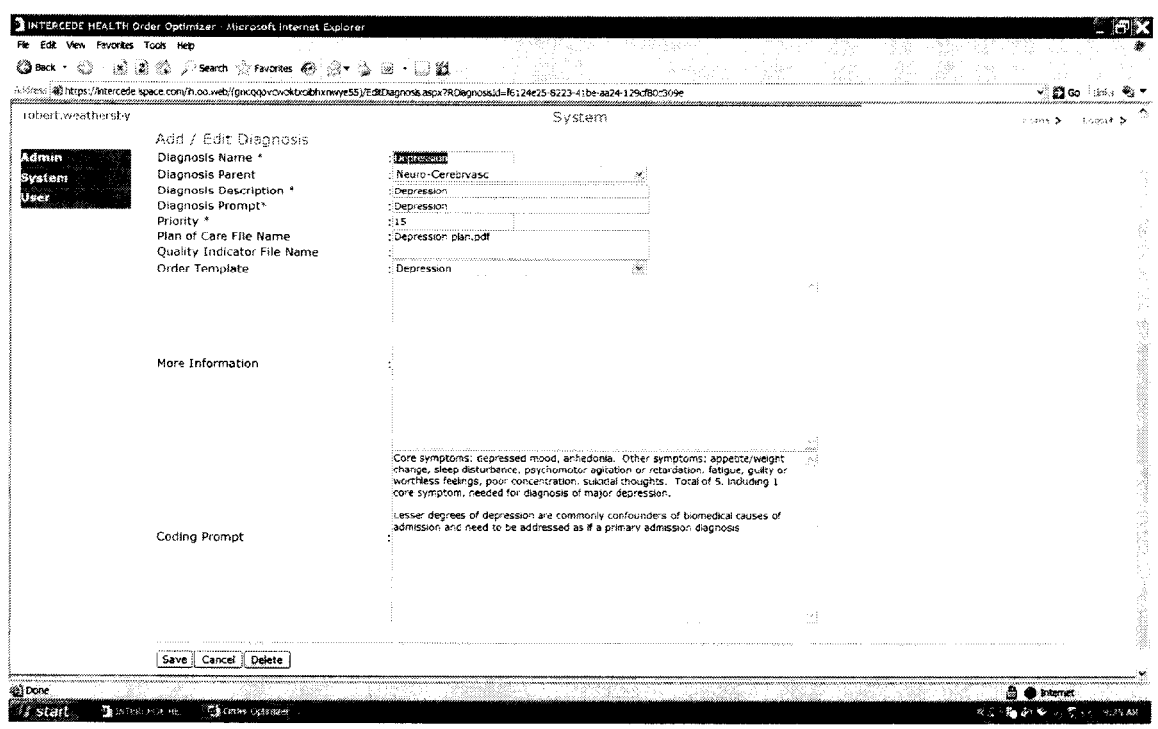
Figure 21:
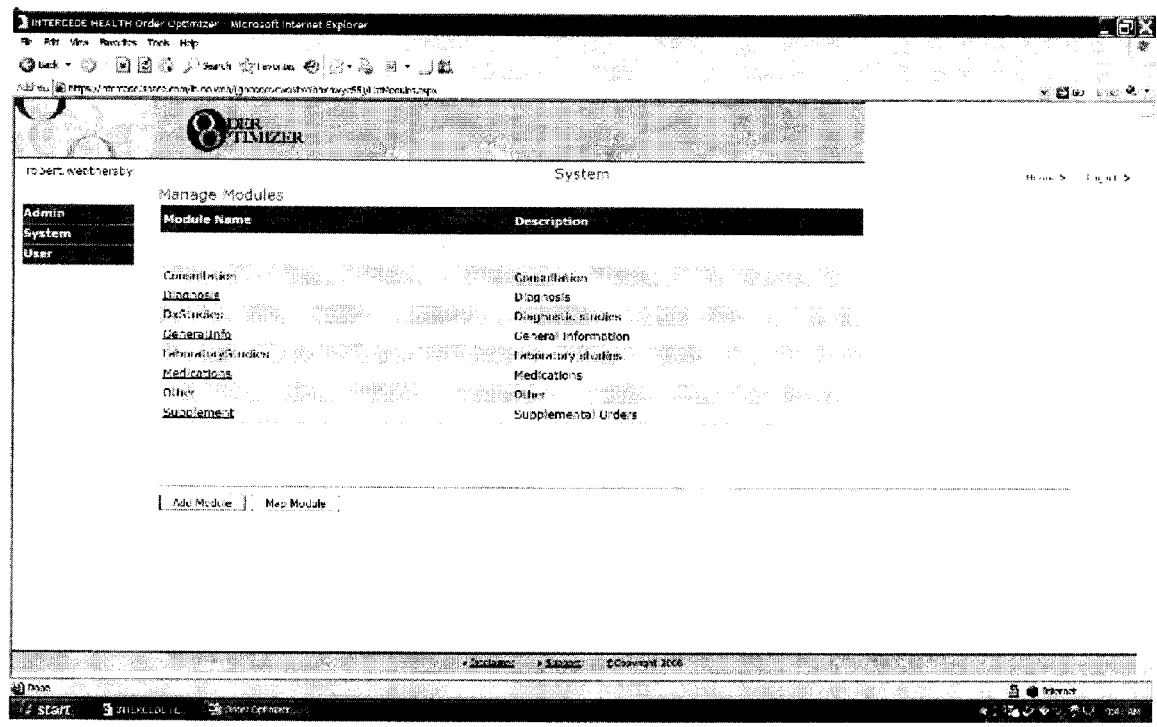
Figure 22:
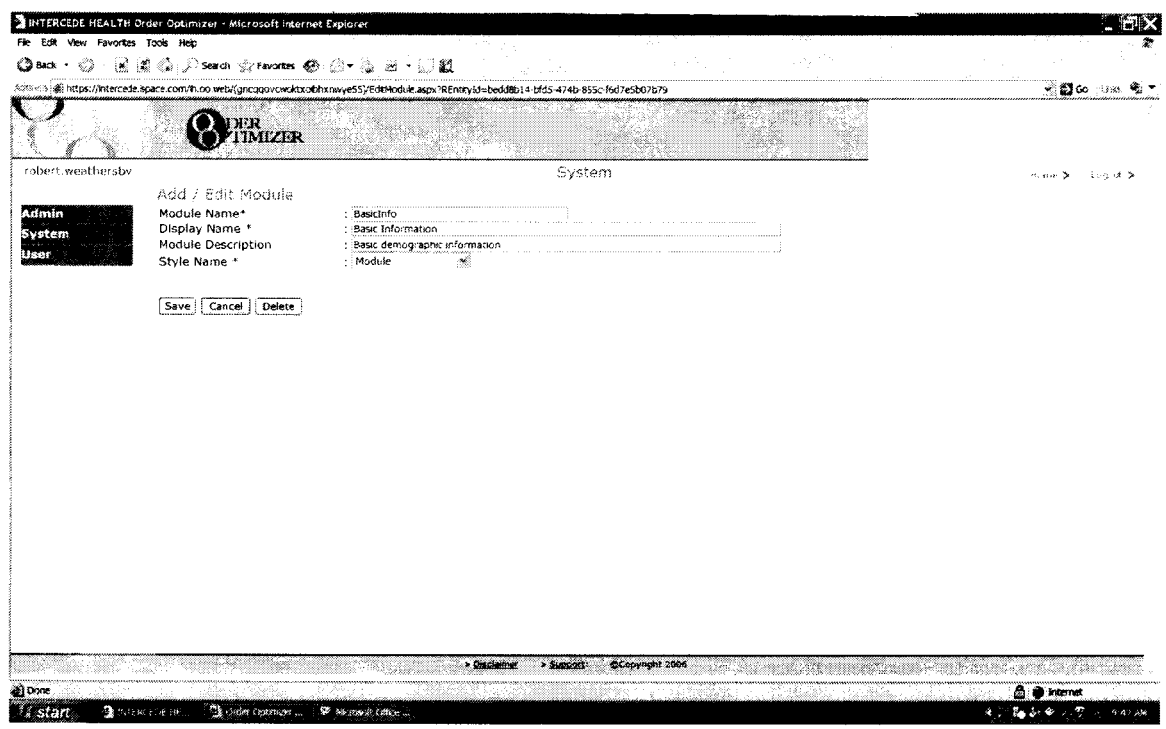
Figure 23:
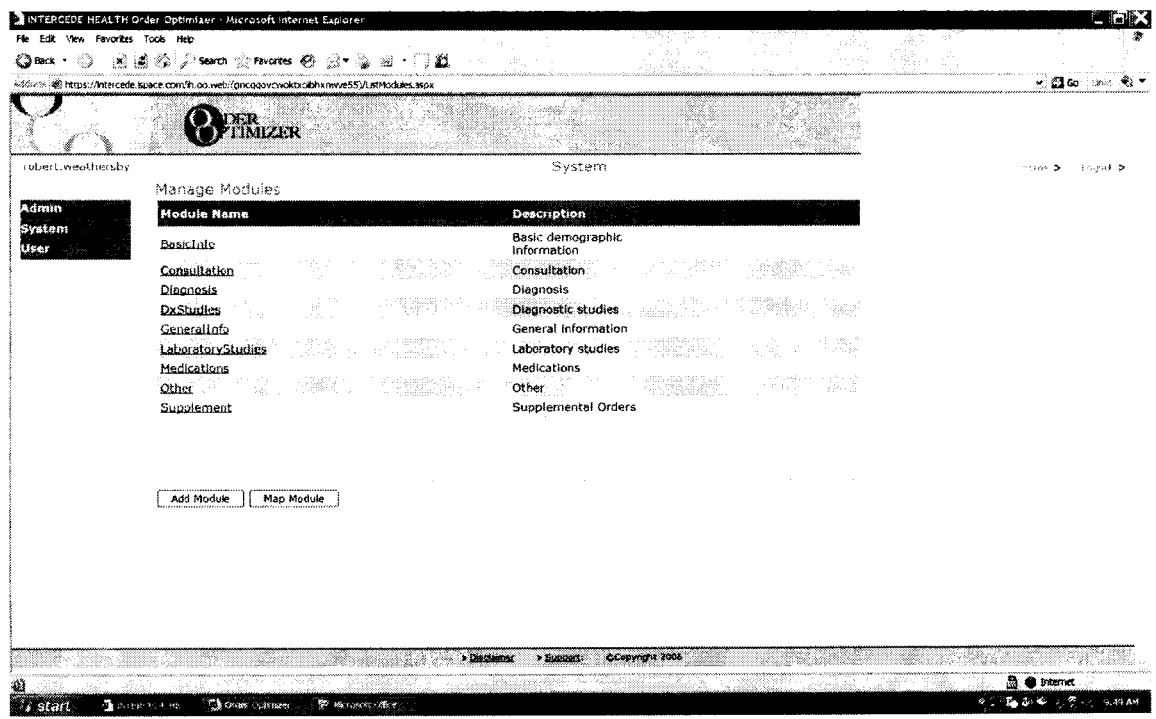

The Admin determines if a new Module is needed, or if an existing one can be reused and/or extended. In this example, a new Module is created called Basic Information—where patient identification information is captured. Once created, this Module can be reused across all Order Set Templates, providing consistency to the Order Sets. Admin is selected from the list on the left of the screen as shown in FIG. 20, resulting in display of the Admin menu. "Manage Modules" is selected from the Admin Menu, and the screen shown in FIG. 21 is displayed. This screen lists all existing Modules. The Admin clicks "Add Module", and is presented with the Add/Edit Module screen (FIG. 22). The Module Name, Description, and its display characteristics are entered as shown. Display characteristics govern appearance characteristics such as font, spacing, etc. Clicking "Save" returns the display to the Manage Modules screen, where the newly created Basic Info module is now displayed as shown in FIG. 23.

Figure 24:
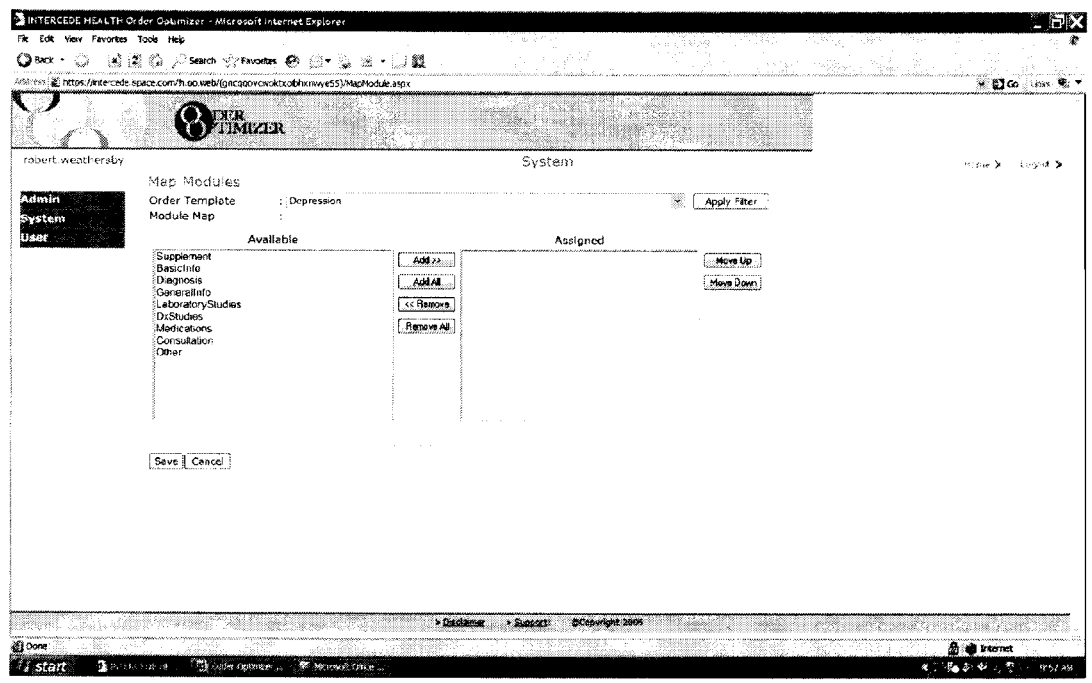
Figure 25:
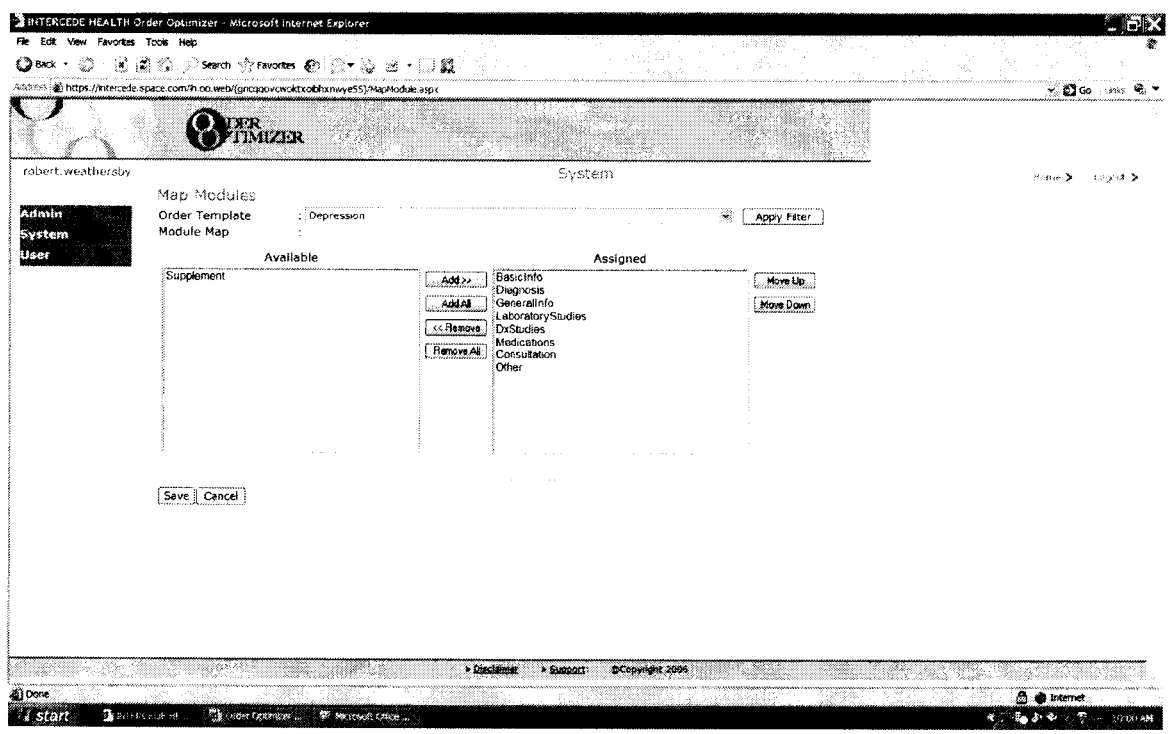

The next step in the present example is to map the new Basic Info Module to the new Order Set Template for Depression. Selecting "Map Modules" from the Manage Modules screen, presents the Map Modules screen as shown in FIG. 24. Here, the user selects his newly created "Depression" Order Set Template, and clicks "Apply Filter". This action causes the system to search its database and retrieve any components available to be attached to an Order Set. These are listed in the list of all available modules in the left hand box. In this example, the new Module of "Basic Info" that was created above, is available to be added to the Depression Order Template, along with other Modules such as Medications, Laboratory Studies, Diagnostics, General Information, Consultations, and Other directives. These previously created Modules can be reused, needing only customization for any attributes unique to the Depression Order Set. Highlighting any of the available modules and selecting the "Add" button assigns the selected module to the Depression Order Set, moving those modules into the right hand box as shown in FIG. 25. Any or all of the available modules can be selected in this way. The "Move Up" and "Move Down" buttons are used to dictate the order in which these Modules will appear on the Order Set. This ordering creates a numeric Display Order value, stored by the system.

Figure 26:
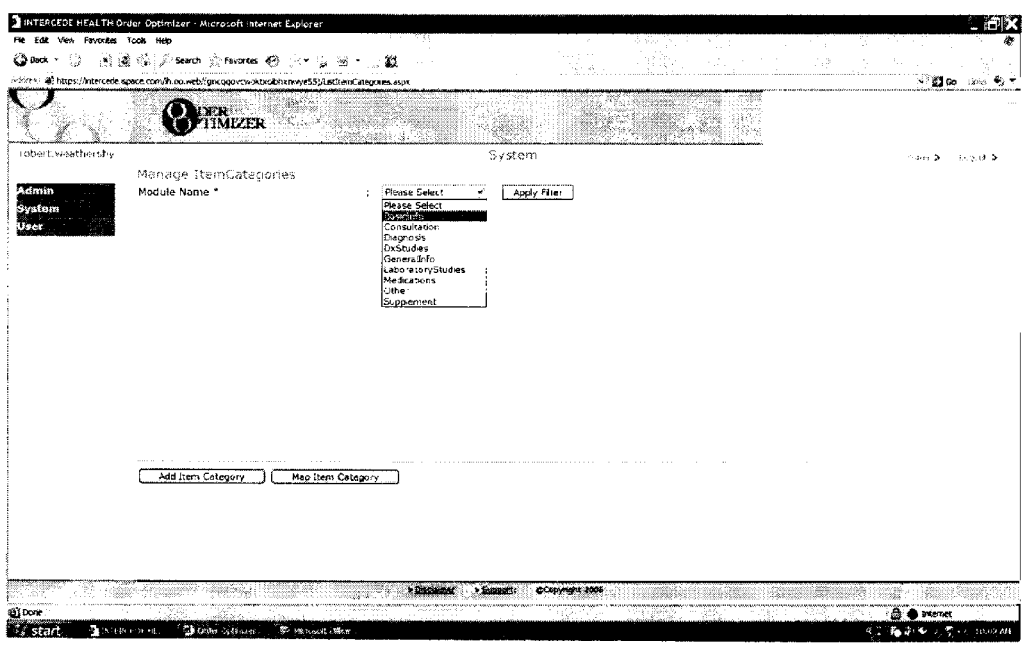

The next step in the example is creating Item categories for the Basic Info Module. Selecting "Manage Item Categories" from the Admin Menu causes the presentation of the Manage Item Categories screen as shown in FIG. 26. Here, the Admin can select the newly created Basic Info Module from the list of available Modules, and click "Apply Filter". This causes the system to retrieve all existing Item Categories available for use in creating Modules, and also allows the Admin to create a new Item Category should the desired one not exist. In the present example, a new Item Category called Admission is created and added to the module "Basic Info." In the example, existing Item Categories, Attending Physician, medical condition, Code Status, Medical Record Number (MRN), Patient Name, and medical professional to notify of the patient's admission are added to the module.

Figure 27:
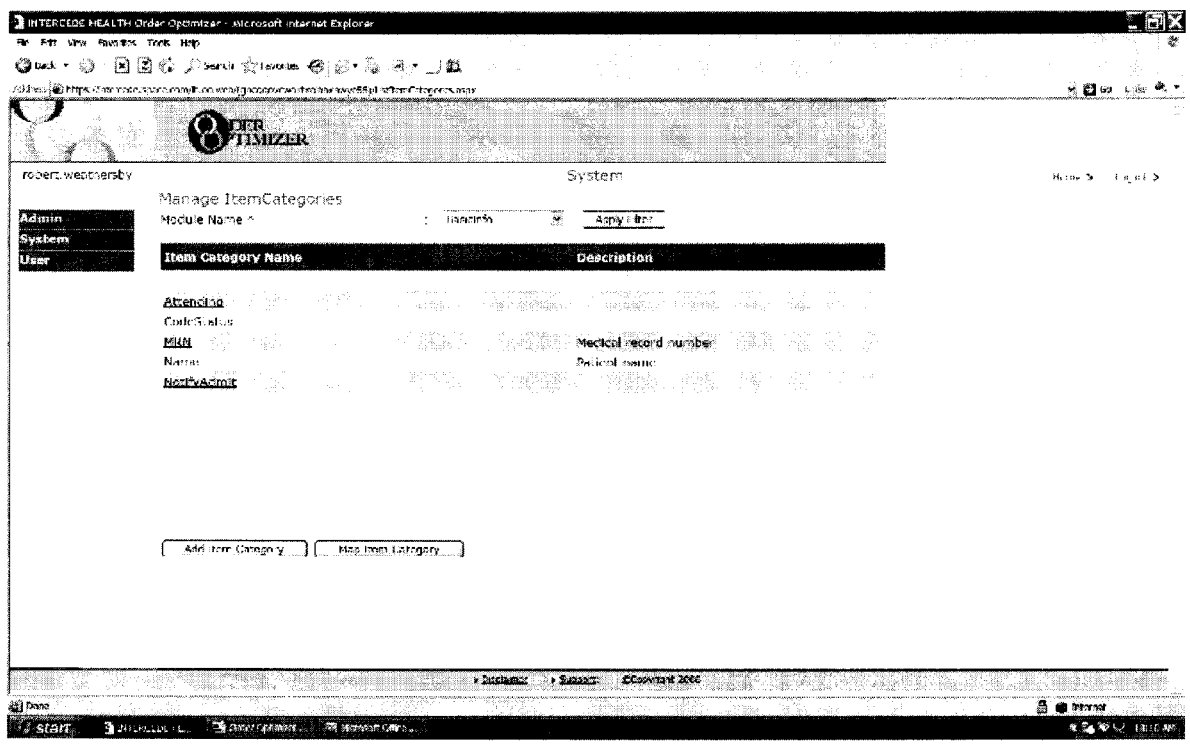
Figure 28:
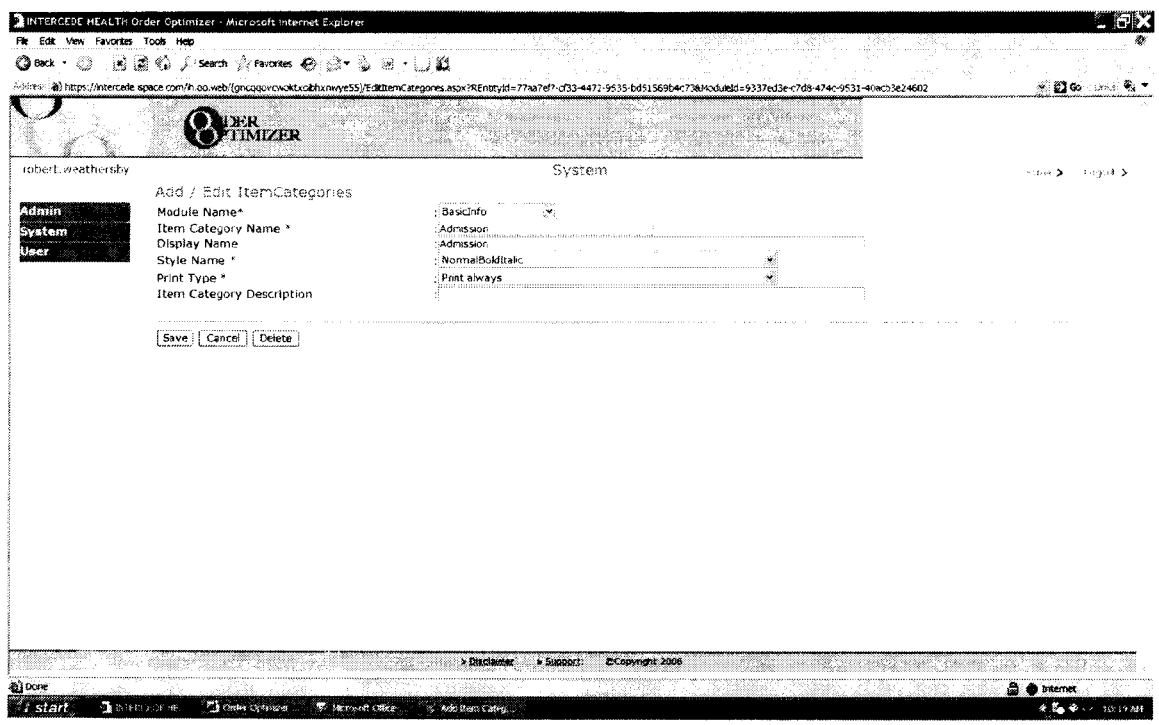
Figure 29:
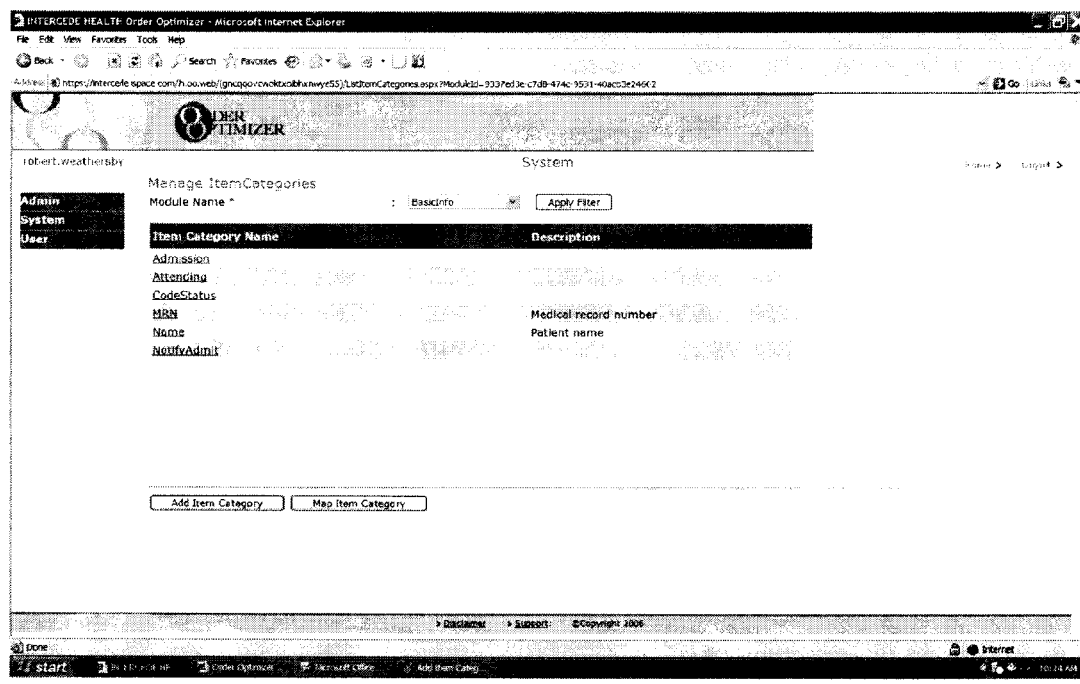
Figure 30:
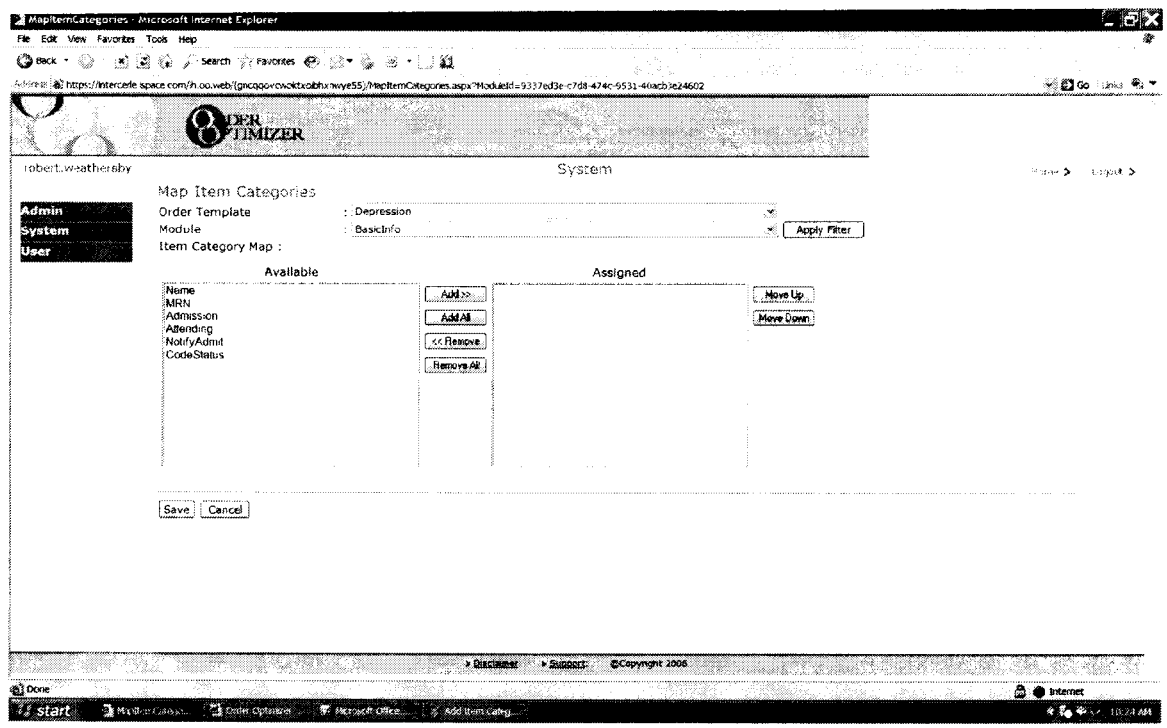
Figure 31:
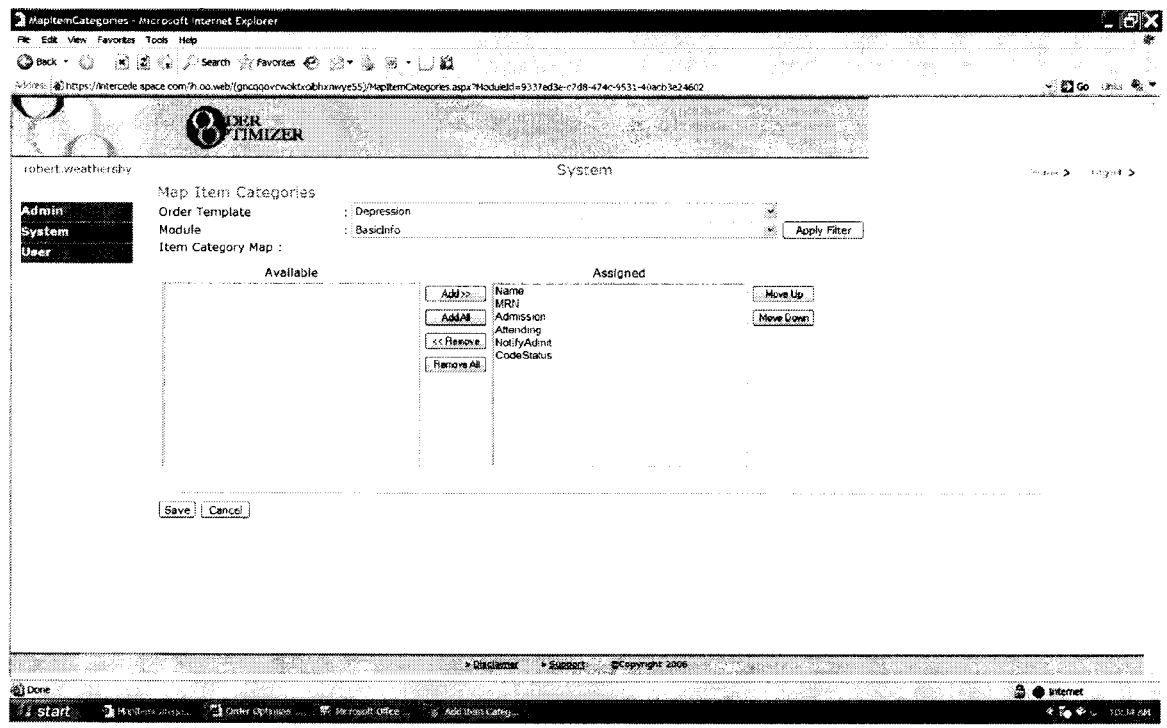
Figure 32:
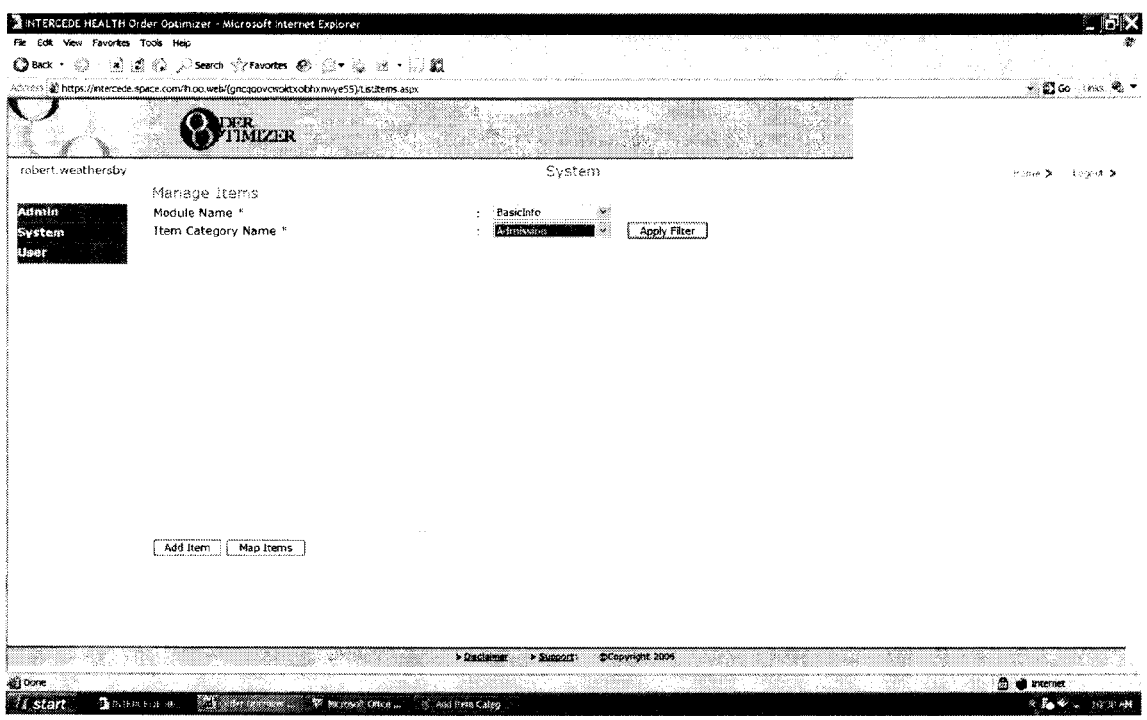

Selecting "Add Item Category" causes the system to display the screen shown in FIG. 27. The module Basic Info is chosen from the list, indicating that the Item Category is to be placed in that module (FIG. 28). The user can enter the Item Category name and desired appearance. Selecting "Save" adds the Item Category, Admission to the list of Item Categories available for the Basic Info Module, and it then appears along with pre-existing Item Categories in the list as shown in FIG. 29. Admission is now available to populate the Basic Info Module. All desired Item Categories can now be added to the Basic Info Module by selecting "Map Item Category", and their Display Order determined. This is done using the Map function, shown in FIG. 30, and also in FIG. 24, when mapping the new Basic Info module within the Depression Order Set template. Here, the newly created Admission Item Category is available to populate the Module, along with other Item Categories. Clicking the "Add" button assigns selected items to the Basic Info Module, or a user can select Add All to assign all available Item Categories to the Basic Info Module as shown in FIG. 31. The "Move Up" and "Move Down" buttons can then be used to dictate the order in which these Modules will appear on the Order Set. When the list is complete and correct, the user selects "Save".

Figure 33:
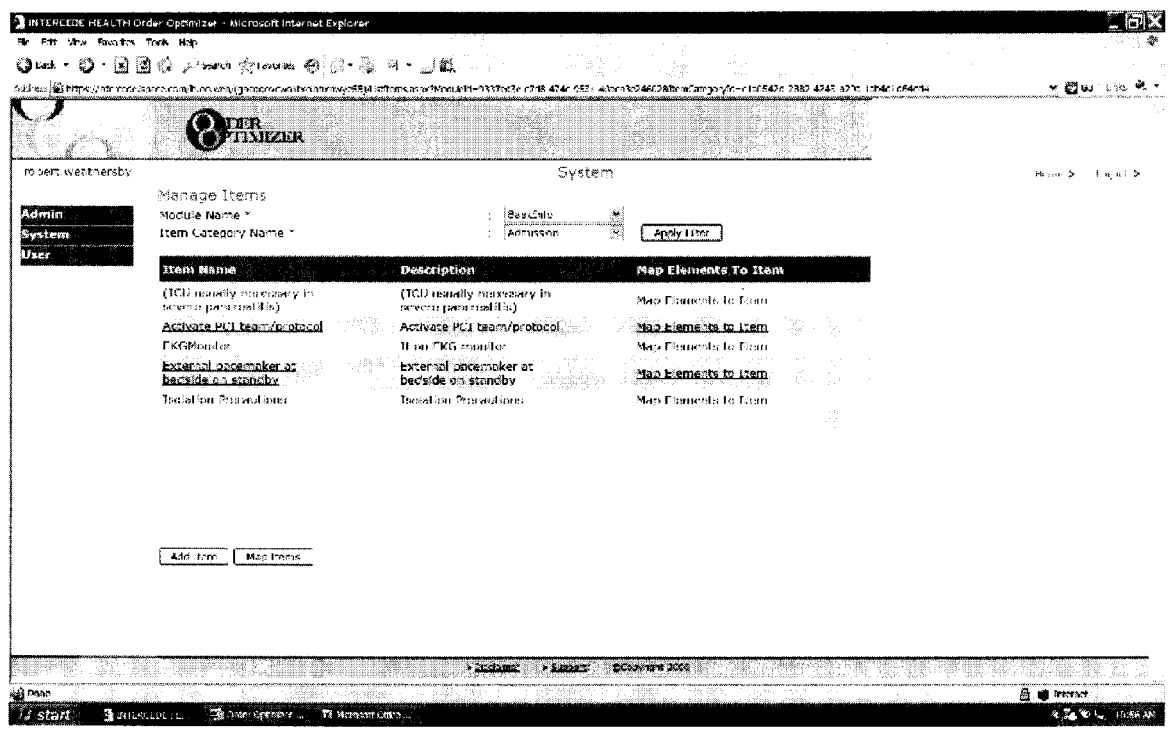
Figure 34:
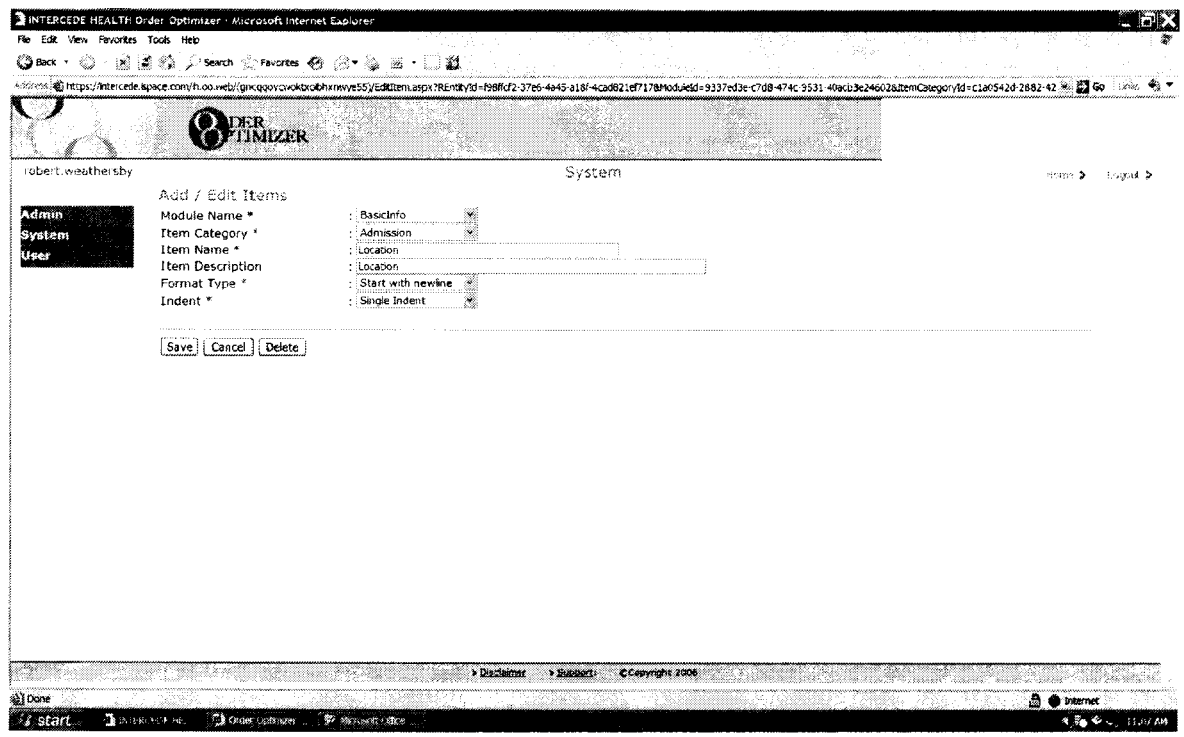
Figure 35:
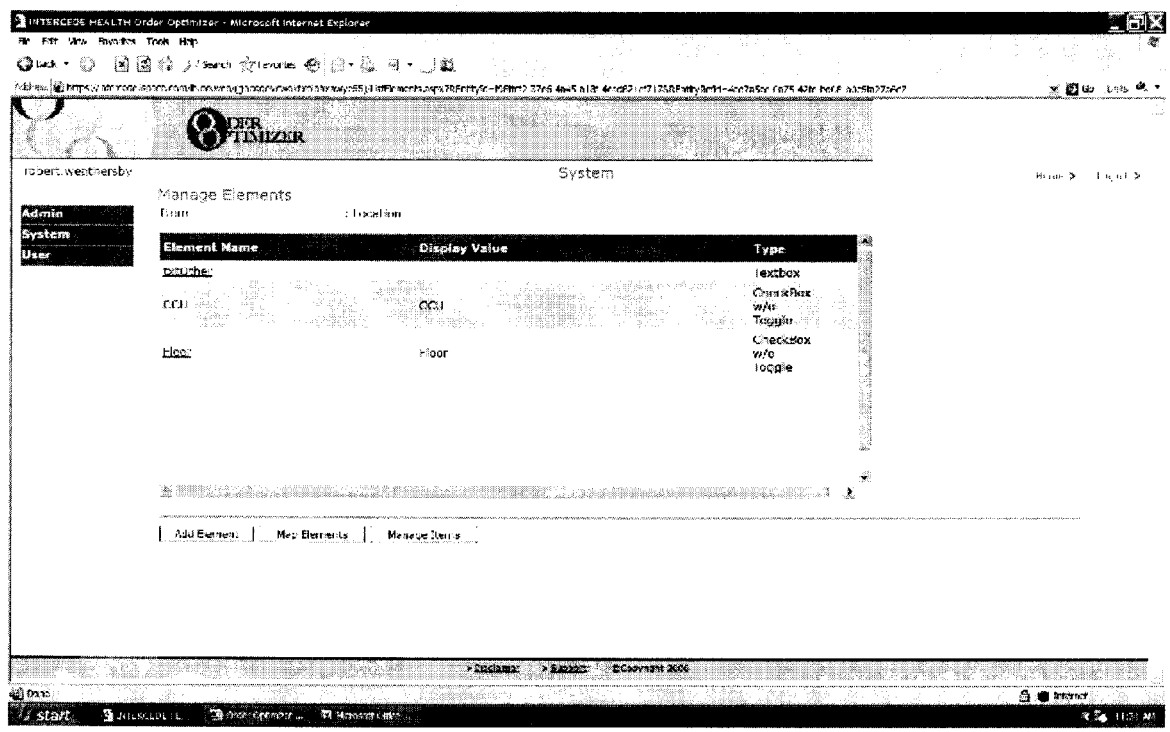
Figure 36:
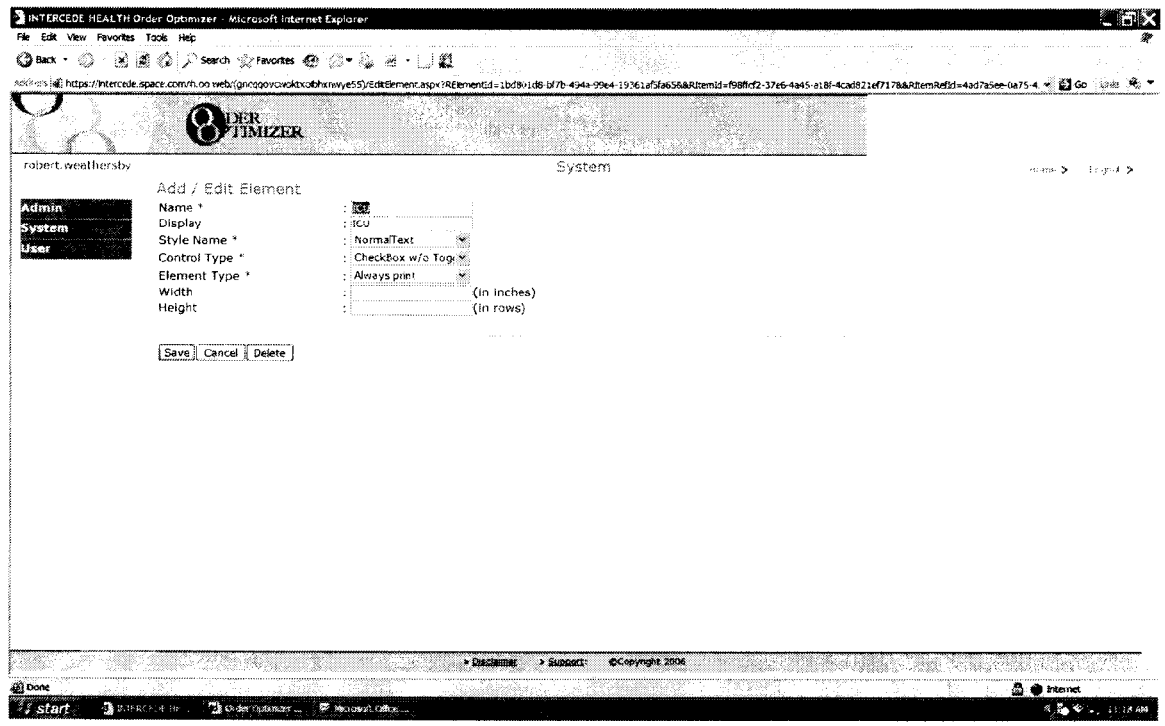

The next step in this example is to add Items to the newly created Admission Item Category. The Items are the descriptive aspects that a Physician considers in determining the exact treatment regimen to prescribe for the patient diagnosis—in this example Depression. Selecting "Manage Items" from the Admin Menu, presents a screen containing a list of existing Modules and Item Category Names. In this example, the user chooses the newly created Module Basic Info from a list of existing Modules, the newly created Item Category Name, Admission, from a list of existing Item Categories, and clicks "Apply Filter" as demonstrated in FIG. 32. The system searches for all Items assigned to this Modules' Item Category, and also allows the Admin to create new Items. For the purposes of this example, a new Item is created to allow a physician to designate to which hospital Location to admit a patient. The "Manage Items" screen is shown in FIG. 33. Selecting "Add Item" present the Admin user with the Add/Edit Items screen, demonstrated in FIG. 34. The Admin user can select the Module, Basic Info and Item Category, Admission, from lists of existing entities. The Admin can then input the Location Admission Item name, and designate its presentation format. Clicking "Save" stores these selections in the database, and returns the Admin user to the Manage Items Screen, where the newly created Item Location is now available to populate the Admission Item Category, along with other existing Items.

The next step in creating the Location Item is creating its input options—determining how the Physician will use this clinical choice. Elements are created by the Admin user to provide those input choices. For example, the Admin user can create an input choice of ICU to allow a physician to designate that a patient should be admitted to the Intensive Care Unit. To create the ICU element, "Manage Element" is selected from the Admin Menu to display the page shown in FIG. 35. Selecting "Add Element" allows the addition of new element, "ICU". The Manage Elements screen, FIG. 36, allows the Admin user to input the descriptive properties of the ICU element, in this example, a label of ICU and a checkbox to allow the physician user to simply check that choice if desired. The Admin user then selects "Save", and returns to the Manage Elements Screen.

Figure 37:
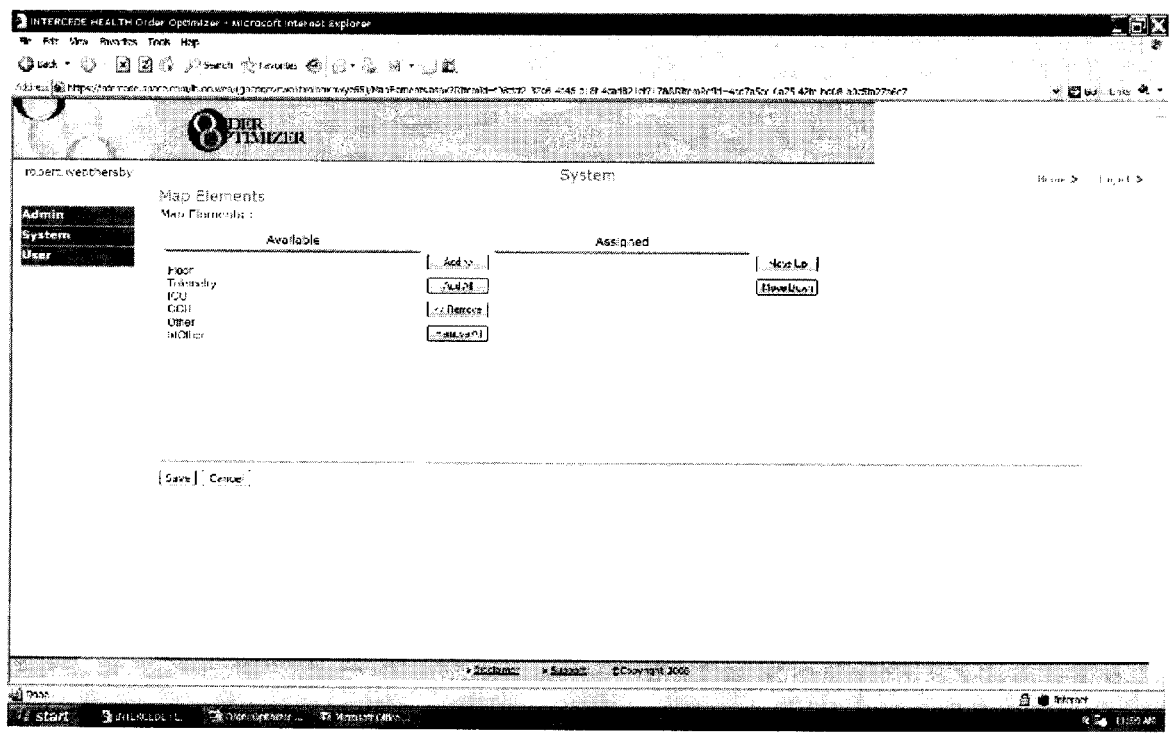
Figure 38:
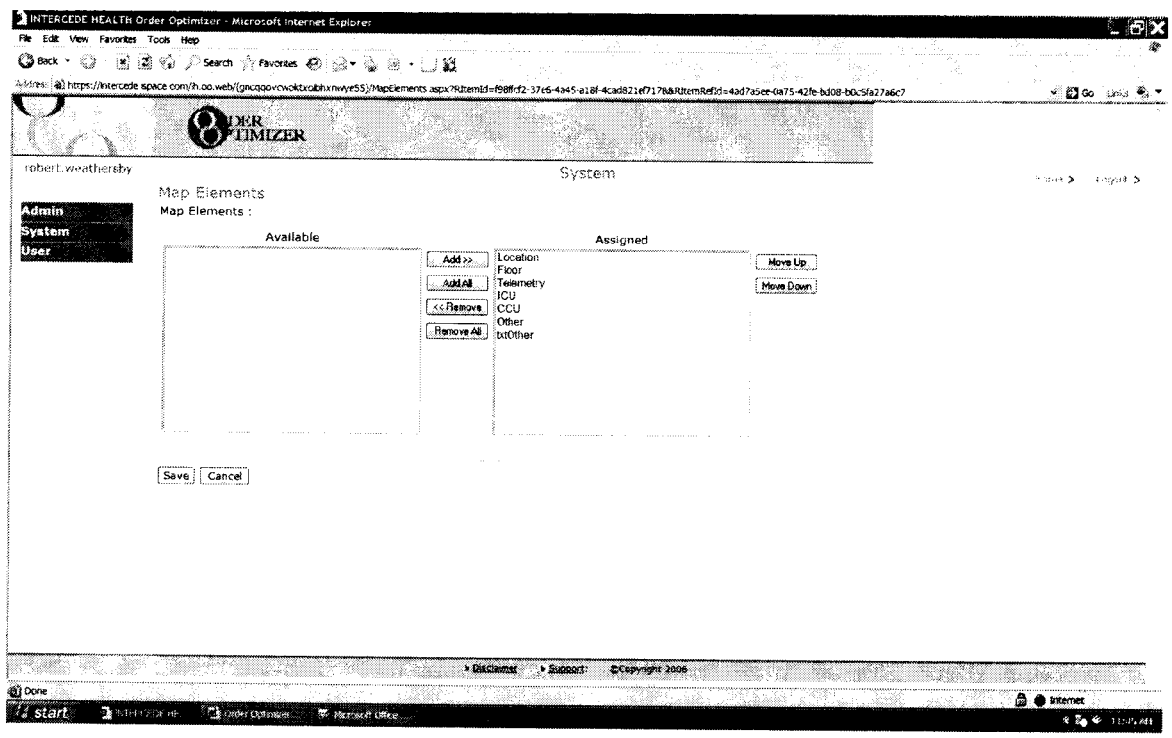

The final step in creating this Item is mapping the newly created Element ICU within the existing Elements as per the Evidence-Based directive. First, the Admin user selects "Map Elements", and is presented with the list of Elements available for inclusion with the Location Item—including the newly created ICU element as shown in FIG. 37. All desired Elements are selected and "Assigned". The "Move Up" or "Move Down" buttons are used to achieve the desired ordering (FIG. 38). Selecting "Save" returns the Manage Elements screen, completing the creation of the Admission Item.

Figure 39:
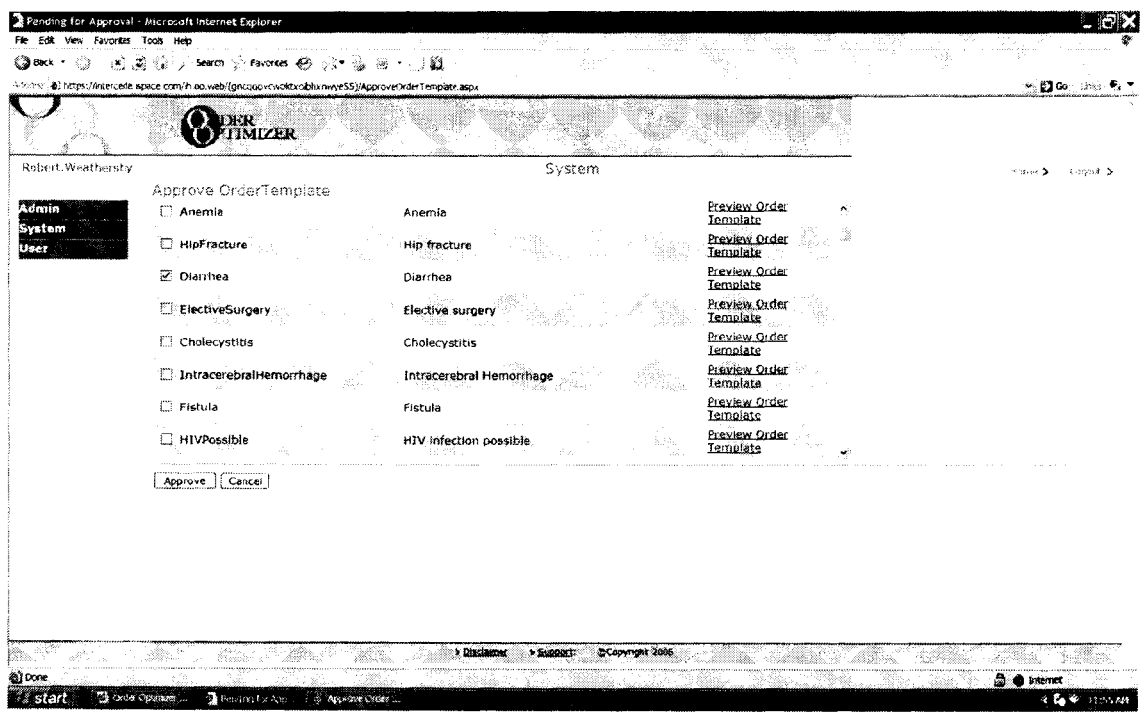

The final step in this example is to approve the Depression Order Set Template. The Admin user selects "Approve Order Templates" from the Admin Menu to view the Approve Order Template page shown in FIG. 39. The Admin user can review the order template, then select the order template such as the Depression Order by clicking the checkbox, for example, and then selecting "Approve". The new Depression Order Set is then available for the physician users.

All of the systems and methods disclosed and claimed herein can be made and executed without undue experimentation in light of the present disclosure. While the systems and methods of these inventions have been described in terms of preferred embodiments, it will be apparent to those of skill in the art that variations may be applied to the systems, system components and/or methods and in the steps or in the sequence of steps of the methods described herein without departing from the concept, spirit and scope of the invention. All such modifications apparent to those skilled in the art are deemed to be within the spirit, scope and concept of the inventions as defined by the appended claims.

The invention claimed is:

1. An electronic system for providing medical orders for a patient, wherein the system comprises:
 a user interface comprising a processor, a monitor and a user input device;
 a memory storage device connected to the user interface processor and comprising a computer readable database, wherein the database comprises protocols for medical orders;
 wherein the database is organized in a hierarchical structure comprising:
 (i) medical order items, each mapped to one or more medical item categories;
 (ii) medical item categories, each comprising medically related items, wherein each item category is mapped to one or more modules; and
 (iii) medical modules, wherein each module is mapped to one or more diagnoses, and wherein each module comprises groups of medical item categories;
 computer readable media containing instructions for providing an interactive display of a list of diagnoses contained in the database, wherein one or more diagnoses are selectable by a user, and including instructions to respond to selection of one or more diagnoses by a user to query the database and retrieve all modules associated with each selected diagnosis and to provide an interactive display of item categories and items within the categories related to each selected diagnosis on the monitor, wherein individual items are selectable by a user; and
 said computer readable media containing instructions for providing an interactive display that, responsive to multiple diagnoses being selected, assigns a display rank to the items for each of the multiple diagnoses by multiplying the sum of each appearance for an item ill all the selected item categories by a first weighting factor and multiplying the number order in which the diagnosis that contains that item was selected by a second, smaller weighting factor; and computer readable media containing instructions for providing an interactive display for selecting generation of an order set, wherein selecting generation of an order set by a user provides a unique set of medical orders for one or more selected diagnoses in which the items are listed in display rank order and repeated items are removed.

2. The system of claim 1, wherein the instructions for assignment of display rank comprises multiplying the number of appearances for an item in all the selected protocols by 1000 and multiplying the number order in which the diagnosis that contains that item was selected by 100, wherein items are displayed in descending order of display rank.

3. The system of claim 1, wherein the medical order items are a pharmaceutical name, a medical directive or a survey question.

4. The system of claim 1, wherein the medical item categories are pharmaceutical agents, laboratory tests, or survey questions.

5. An electronic system for providing medical orders for a patient, wherein the system comprises:
   a server computer connectable to a user interface;
   a computer readable memory connected to the server computer comprising one or more databases for storing client information;
   a computer readable memory connected to the server computer comprising one or more databases for storing patient information; and
   a computer readable memory comprising a database connected to the server computer, wherein the database comprises protocols for medical treatments organized by diagnoses, wherein each protocol comprises a plurality of orders;
   wherein the database is organized in a hierarchical structure comprising;
   (i) medical order items, each mapped to one or more medical item categories;
   (ii) medical item categories, each comprising medically related items, wherein each item category is mapped to one or more modules; and
   (iii) medical modules, wherein each module is mapped to one or more diagnoses, and wherein each module comprises groups of medical item categories;
   wherein the server comprises;
   computer readable media with embedded instructions for receiving user information from the user interface and for sending or retrieving information about a user to or from the client information database;
   computer readable media with embedded instructions for receiving patient information from the user interface and for sending or retrieving information about a patient to or from the patient information database;
   computer readable media with embedded instructions for receiving a request to display a list of diagnoses to the user interface upon receipt of a request for diagnoses from the user interface;
   computer readable media with embedded instructions for receiving selections of one or more diagnoses from the user interface, for retrieving protocols for the selected one or more diagnoses from the current protocol database, prioritizing the orders within the set of selected diagnoses such that the orders are ranked by number of occurrences within the set of selected diagnoses and by order of selection of diagnosis, and wherein repeated orders are removed, and transmitting the prioritized unique orders to the user interface;
   computer readable media with embedded instructions for receiving selections and modifications of orders from the user interface, removing non-selected orders, and transmitting an order set to the user interface.

6. The system of claim 5, wherein the server is connected to the user interface by an intranet connection.

7. The system of claim 5, wherein the server is connected to the user interface by an internet connection.

8. The system of claim 5, wherein the system resides in a stand alone computer.

9. The system of claim 5, wherein the instructions for prioritizing the orders within a set of diagnoses includes assignment of display rank by multiplying the number of appearances for an item in all the protocols by 1000 and multiplying the number order that the diagnosis was selected that contains that item by 100, wherein items are displayed in descending order of display rank.

10. The system of claim 5, wherein the patient is hospitalized.

11. The system of claim 5, wherein the patient is being released from a hospital.

12. The system of claim 5, wherein the current protocol database include support material associated with at least one diagnosis, wherein the support material includes information about the diagnosed condition and its treatment, coding information about the diagnosis or a combination thereof.

13. The system of claim 5, wherein the medical order items are a pharmaceutical name, a medical directive or a survey question.

14. The system of claim 5, wherein the medical item categories are pharmaceutical agents, laboratory tests, or survey questions.

15. An electronic system for providing medical orders for a patient, wherein the system comprises:
   a user interface comprising a processor, a monitor and a user input device;
   a memory storage device connected to the user interface processor and comprising a computer readable database, wherein the database comprises protocols for medical treatments;
   computer readable media containing instructions for providing an interactive display of a list of names of diagnoses contained in the database,
   computer readable media containing instructions to receive a user input of selection of one or more diagnoses,
   wherein the database is organized in a hierarchical structure comprising;
   (i) medical order items, each mapped to one or more medical item categories;
   (ii) medical item categories, each comprising medically related items, wherein each item category is mapped to one or more modules; and
   (iii) medical modules, wherein each module is mapped to one or more diagnoses, and wherein each module comprises groups of medical item categories;
   computer readable media containing instructions to display an order set comprising a list of order categories and order items within each order category;
   computer readable media containing instructions to recognize when multiple diagnoses are selected, and to display the orders within each order category according to the display rank for each order within the categories;

wherein the display rank for an order item is the sum of (i) the total number of times the order item appears in all the selected diagnoses multiplied by a first weighting factor and (ii) the number of the diagnosis selection order for the first diagnosis to contain that order item, with the first selected diagnosis receiving the highest selection order number and the last selected diagnosis receiving the lowest selection order number, wherein the selection order number is multiplied by a second, lesser weighting factor;

computer readable media containing instructions to remove duplicate orders; and computer readable media containing instructions to display the unique order items in display rank order from highest to lowest in an order set format.

16. The system of claim 15, wherein the medical order items are a pharmaceutical name, a medical directive or a survey question.

17. The system of claim 15, wherein the medical item categories are pharmaceutical agents, laboratory tests, or survey questions.

18. A method of providing a merged set of medical orders for treatment of a patient with multiple diagnoses or conditions comprising:

selecting, on an electronic system, one or more diagnoses or conditions from a list of diagnoses and conditions;

identifying a set of orders for treatment or management of a patient with a selected diagnosis or condition;

electronically associating the set of orders with one or more diagnoses or conditions in the list of diagnoses and conditions;

displaying the associated set of orders to a user on an electronic interface for the user to review the displayed associated set of orders;

the user selecting, via the electronic interface, one or more orders for a patient;

assigning, via a computer system, a display rank to each of the selected orders in which the display rank is calculated by multiplying the total number of appearances of the order within all the selected diagnoses or conditions by a first weighting factor and multiplying the order number of selection of the diagnosis or condition in which the order appears by a second, lower weighting factor, and summing the two numbers to assign a display rank to each order;

removing, via the computer system, duplicate orders from the ranked order list; and electronically displaying the orders that are associated with all the selected diagnoses or conditions in display rank order irrespective of the diagnosis or condition with which the order is associated.

\* \* \* \* \*